United States Patent [19]
Fujimoto et al.

[11] Patent Number: 6,055,972
[45] Date of Patent: May 2, 2000

[54] AIR FUEL RATIO CONTROL APPARATUS HAVING AIR-FUEL RATIO CONTROL POINT SWITCHING FUNCTION

[75] Inventors: Masaya Fujimoto, Kariya; Minoru Ohta, Okazaki; Makoto Nakae, Toyoake; Isao Watanabe, Nagoya; Naoto Miwa, Tsushima; Hiromi Sano; Masahiro Shibata, both of Nagoya, all of Japan

[73] Assignee: Denso Corporation, Kariya, Japan

[21] Appl. No.: 08/886,063

[22] Filed: Jun. 30, 1997

[30] Foreign Application Priority Data

| Jul. 4, 1996 | [JP] | Japan | 8-174960 |
| Jul. 19, 1996 | [JP] | Japan | 8-209287 |
| Jun. 9, 1997 | [JP] | Japan | 9-168075 |

[51] Int. Cl.[7] .................................................. F02D 41/30
[52] U.S. Cl. ................................... 123/688; 123/697
[58] Field of Search ........................ 123/693, 697, 123/685, 686, 688, 694, 703; 60/274, 285

[56] References Cited

U.S. PATENT DOCUMENTS

| 4,543,176 | 9/1985 | Harada et al. ........................ 204/406 |
| 5,544,640 | 8/1996 | Thomas et al. ........................ 123/689 |
| 5,709,198 | 1/1998 | Sagisaka et al. ...................... 123/684 |

FOREIGN PATENT DOCUMENTS

| B2-52-13584 | 4/1977 | Japan . |
| 63-223347 | 9/1988 | Japan . |
| 6-294340 | 10/1994 | Japan . |

Primary Examiner—Thomas N. Moulis
Assistant Examiner—Mahmoud M Gimie
Attorney, Agent, or Firm—Nixon & Vanderhye P.C.

[57] ABSTRACT

An air-fuel ratio sensor of a limit current type is used for an air-fuel ratio feedback control. When the air-fuel ratio sensor is in a semi-activated state, the air-fuel ratio sensor is driven into an electromotive force generating mode by a current externally applied thereto thereby to shift an electromotive force changing point so that an air-fuel ratio at which the electromotive force changes stepwise is shifted from the stoichiometric ratio point to a lean zone. When the air-fuel ratio sensor is in a completely activated state, the air-fuel ratio sensor is applied with a voltage to produce a limit current varying with an air-fuel ratio so that a feedback control is performed based on the advanced control theory by using a linear current output characteristics.

19 Claims, 19 Drawing Sheets

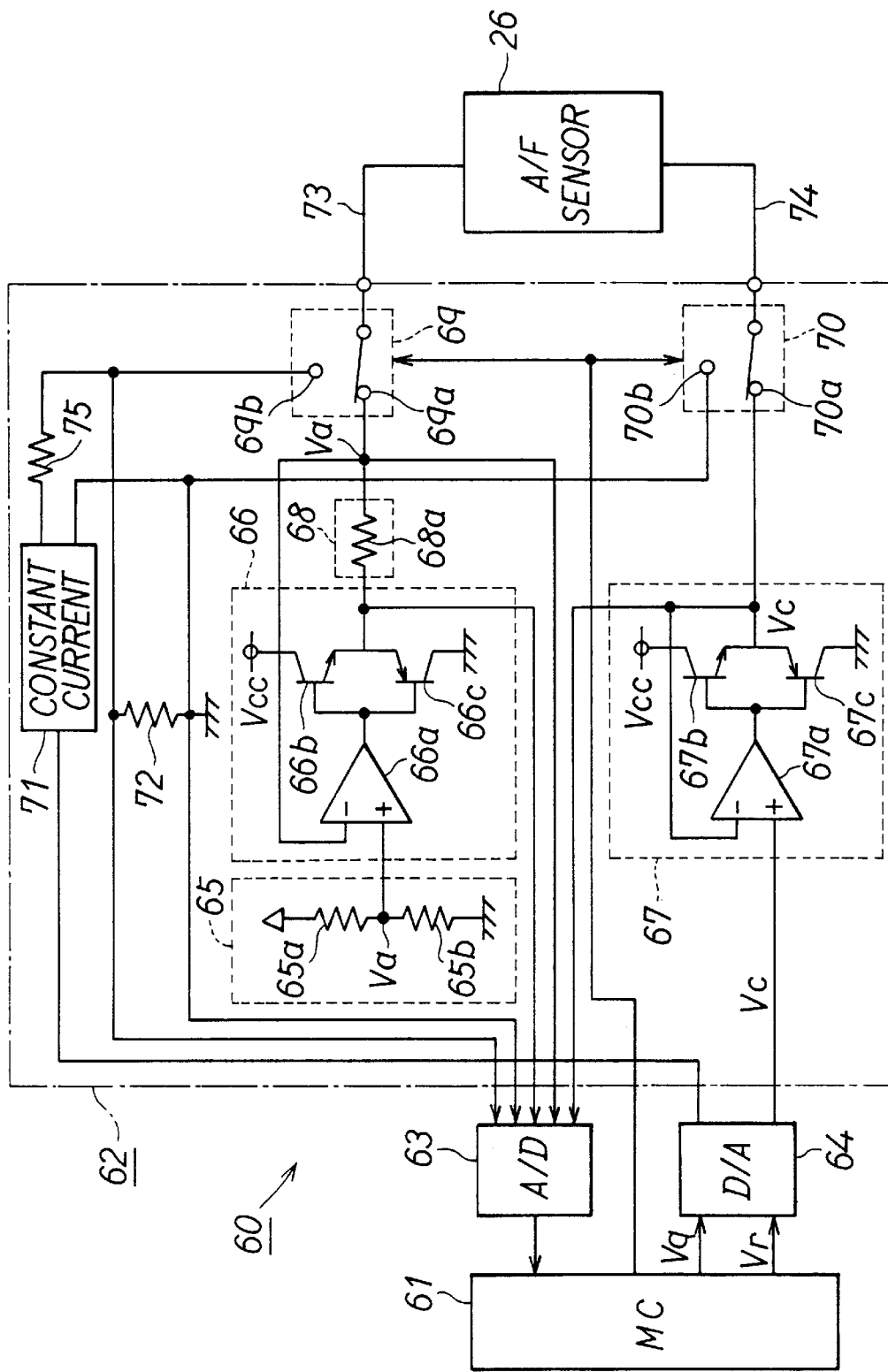

AIR FUEL RATIO CONTROL APPARATUS HAVING AIR-FUEL RATIO CONTROL POINT SWITCHING FUNCTION

BACKGROUND OF THE INVENTION

1. Field of the Invention

The present invention relates to an air-fuel ratio control apparatus for an internal combustion engine and, more particularly, to an air-fuel ratio control apparatus which switches the air-fuel ratio control point.

2. Related Art

As a conventional technology of this type, a control apparatus is disclosed in Japanese Patent Laid-open No. Sho 63-223347 wherein, with an air-fuel ratio sensor heated to a semi-activated state, feedback control of the air-fuel ratio is implemented by detecting an electromotive force output by the sensor in accordance with a Z-characteristics (stepwise output change) of the sensor. In this case, feedback control is controlled to the stoichiometric air-fuel ratio used as a target. In addition, with the air-fuel ratio sensor heated to a complete activated state, feedback control of the air-fuel ratio is implemented by detecting a limit current output by the sensor in accordance with linear characteristics of the sensor.

In recent years, however, there is a tendency that the exhaust gas regulations are in a process of being enforced, giving rise to problems that, with the substantial known technology for carrying out control based on the stoichiometric air-fuel ratio in the semi-activated state, a satisfactory effect of sufficient emission reduction and maintenance of good drivability can not be obtained. In particular, the problems are observed strikingly right after a cold-start of the internal combustion engine, a start of the engine at a low temperature.

In addition, even with the air-fuel ratio sensor heated to the semi-activated state, there has been recently raised a demand for control of the air-fuel ratio to a value located on a lean side (or a rich side) to a certain degree in close proximity to the stoichiometric air-fuel ratio point in an attempt to reduce the emission and maintain the good drivability described above. However, the existing air-fuel ratio control apparatus does not respond satisfactorily to such a demand, giving rise to a problem of the necessity to normally wait until the air-fuel ratio sensor is heated to the complete activated state.

In the case of an air-fuel ratio sensor that has only the Z-characteristics changing its output stepwisely at the stoichiometric air-fuel ratio point such as an oxygen sensor, the amount of injected fuel is controlled to a value on the rich side during heavy load driving at a high speed or the amount of injected fuel is likewise controlled to a value on the rich side in order to prevent the catalyst from being overheated. In this case, the feedback control of the air-fuel ratio can not be continued. Therefore, an open-loop control is enforced temporarily, leading to a variety of problems such as noxious exhaust emission.

It should be noted that, as a method of controlling the air-fuel ratio by using an air-fuel ratio sensor of the limit current type, that is, an air-fuel ratio sensor which generates a limit current, a method for controlling the operation of an internal combustion engine in a lean zone aimed at reduction of the fuel consumption and reduction of the amount of NOx (nitrogen oxides) instead of control based to the stoichiometric air-fuel ratio (air excess ratio $\lambda=1$) has also been disclosed in Japanese Patent Laid-open No. Sho 58-158553.

SUMMARY OF THE INVENTION

The present invention addresses the problems described above and has an object to provide an air-fuel ratio control apparatus for an internal combustion engine capable of reducing noxious exhaust emission and maintaining good drivability.

The present invention has another object to improve air-fuel ratio control characteristics wherein, by changing the electromotive force characteristics of an air-fuel ratio sensor, an air-fuel ratio feedback can be started quickly and the air-fuel ratio control to other than a stoichiometric air-fuel ratio point can be carried out.

According to a first aspect of the present invention, an air-fuel ratio control apparatus is provided with an air-fuel ratio sensor comprising a solid electrolyte layer and at least a pair of electrodes provided on both sides of the solid electrolyte layer and used for generating an electromotive force which changes stepwisely in a zone in close proximity to the stoichiometric air-fuel ratio point when no forced current is supplied externally to the air-fuel ratio sensor. Electromotive force characteristics of the air-fuel ratio sensor can be changed to characteristics with an air-fuel ratio, at which the electromotive force changes stepwisely, shifted from the stoichiometric air-fuel ratio point to a lean or rich zone as a result of supplying the forced current externally source from one of the electrodes to the other. Feedback control of an air-fuel ratio is implemented by using the changed electromotive force characteristics to determine whether the air-fuel ratio detected by the air-fuel ratio sensor is on the lean or rich zone with respect to the air-fuel ratio point of the changed electromotive force characteristics at which the electromotive force changes stepwisely.

That is, the electromotive force characteristics can be changed from time to time arbitrarily in accordance with a target air-fuel ratio suitable for the operating conditions of the internal combustion engine, allowing the feedback control to the air-fuel ratio different from the stoichiometric air-fuel ratio point. When the electromotive force characteristics are changed to characteristics exhibiting stepwise change in the electromotive force at an air-fuel ratio in a lean zone at the start of the internal combustion engine, for example, by implementing feedback control based on these changed electromotive force characteristics, the amount of HC exhausted at the start of the internal combustion engine can be reduced. In addition, with the electromotive force characteristics changed to characteristics exhibiting an stepwise change in electromotive force at an air-fuel ratio in a rich zone during acceleration following the completion of the warming-up of the internal combustion engine, by implementing feedback control based on these changed electromotive force characteristics, the feedback control can be continued even during an operation of the internal combustion engine under a heavy load.

According to another aspect of the present invention, in an air-fuel ratio control apparatus, when an air-fuel ratio sensor is in the semi-activated state, the electromotive force characteristics of the air-fuel ratio sensor are changed to characteristics in which the electromotive force changes abruptly, shifted from the stoichiometric air-fuel ratio point to a lean or rich zone by supplying a forced current externally. In this case, the characteristics to which the electromotive force characteristics are changed in the semi-activated state of the air-fuel ratio sensor is determined by using the characteristics and specifications of the internal combustion engine as a base.

When the air-fuel ratio sensor is in the semi-activated state, it is desirable to implement first feedback control of the air-fuel ratio wherein the changed electromotive force characteristics are used for determining whether a detected air-fuel ratio is on the lean or rich zone with respect to the air-fuel ratio of the changed electromotive force characteristics. It is also desirable to implement second feedback control of the air-fuel ratio by using a detected air-fuel ratio when the air-fuel ratio sensor is in the complete activated state.

That is, as the air-fuel ratio sensor undergoes activation process, the air-fuel ratio control switches from the first feedback control to the second feedback control. It should be noted that the second feedback control is PI control of the air-fuel ratio in a zone around the stoichiometric air-fuel ratio or feedback control of the air-fuel ratio based on the advanced control theory over a relatively wide air-fuel ratio range.

In this case, during a period of time between the start of the internal combustion engine and the completion of activation of the air-fuel ratio sensor, feedback control at a desired air-fuel ratio according to the specifications of the internal combustion engine can be implemented even if the air-fuel ratio sensor is still in a state prior to the complete activation, that is, in a semi-activated state. As a result, it is possible that the control to the desired air-fuel ratio can be started at the earliest time and, at the same time, the emission can be reduced as well as good drivability can be maintained.

Preferably, in the above aspects of the present invention, the electromotive force characteristics of the air-fuel ratio sensor are changed by the forced current from a atmosphere-side electrode to an exhaust-side electrode of the air-fuel ratio sensor, or oppositely by the forced current from the exhaust-side electrode to the atmosphere-side electrode. Thus, the electromotive force characteristics representing a relation between the air-fuel ratio and the electromotive force can be changed with ease. In addition, the air-fuel ratio at which the electromotive force changes abruptly, can be shifted over a relatively wide range. In the case of the stoichiometric air-fuel ratio of 14.7, for example, the electromotive force characteristics can be shifted over an air-fuel ratio range of ±3.

Preferably, the air-fuel ratio sensor is a limit current generating type that has first characteristics, the electromotive force characteristics exhibiting a stepwise change in electromotive force output at the stoichiometric air-fuel ratio point, and second characteristics exhibiting linear changes in current output by the application of a predetermined voltage between the electrodes provided on both the sides of the solid electrolyte. The first characteristics can be changed by controlling a current flowing from one of the electrodes of the air-fuel ratio sensor to the other electrode. In this case, implementation of the first feedback control of the air-fuel ratio is based on the changed first characteristics and implementation of the second feedback control of the air-fuel ratio is based on the second characteristics.

With the configuration described above, even in the case of an air-fuel ratio sensor with a relatively high activation temperature such as a limit current generating air-fuel ratio sensor with an activation temperature of about 650 degrees Celsius, desired feedback control of the air-fuel ratio can be implemented at the earliest time.

Preferably, the determination on the activation state of the air-fuel ratio sensor is made based on either one of quantities such as a time lapsing from a start of the internal combustion engine, the level of the electromotive force generated by the air-fuel ratio sensor, a sensing element resistance of the air-fuel ratio sensor, a sensing element temperature of the air-fuel ratio sensor and an amount of power supplied to a heater provided in the air-fuel ratio sensor since the start of the internal combustion engine, or a combination of the quantities. As a result, the determination on the activation state of the air-fuel ratio sensor can be made with ease and with a high degree of reliability.

BRIEF DESCRIPTION OF THE DRAWINGS

The embodiments of the present embodiment will be described with reference to the accompanying drawings, wherein:

FIG. 5 is a circuit diagram showing a sensor driving unit employed in the first embodiment;

DETAILED DESCRIPTION OF THE PREFERRED EMBODIMENTS

Figure 1:
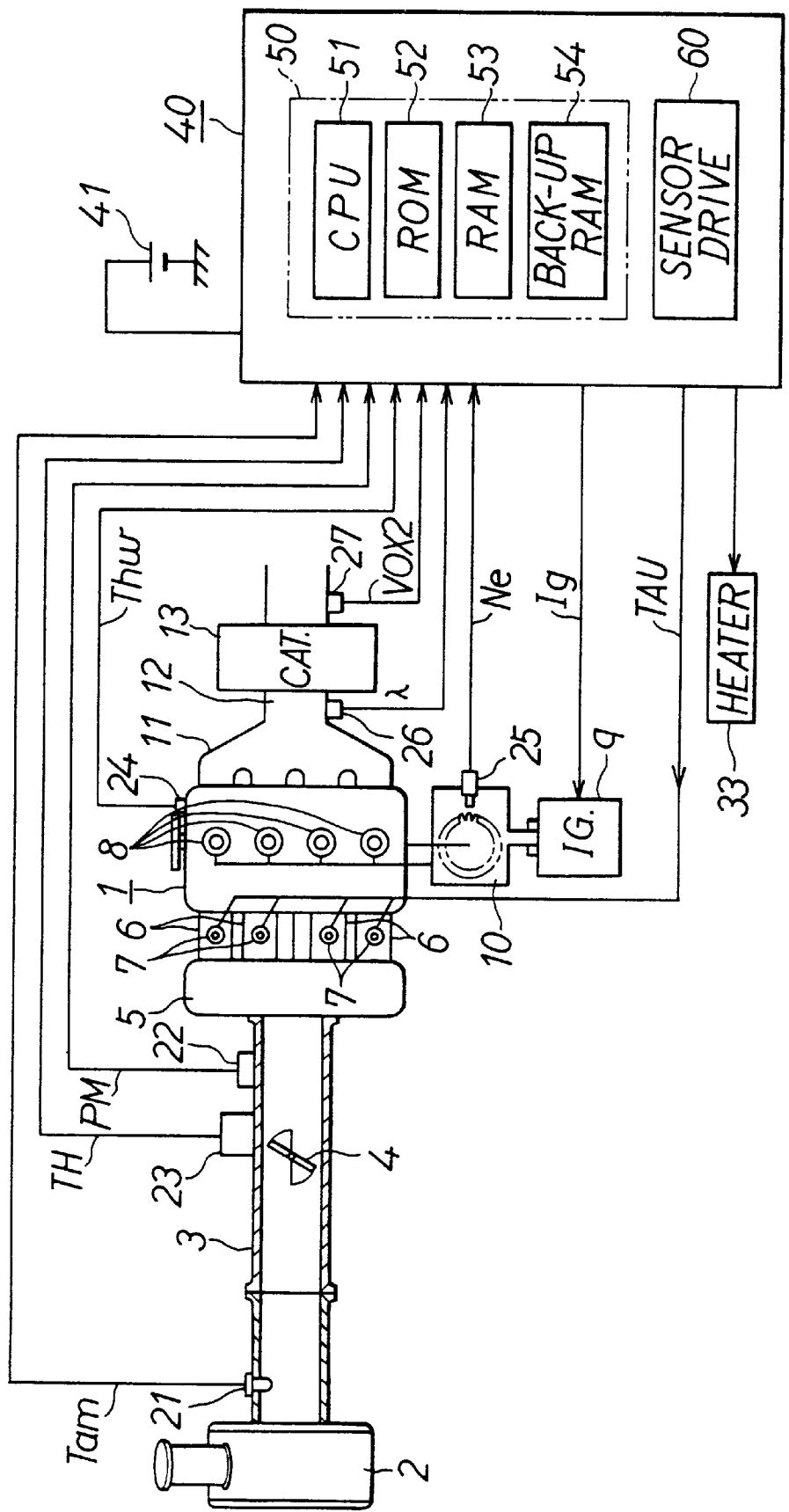
FIG. 1 is a schematic view showing an overall configuration of an air-fuel ratio control apparatus according to a first embodiment of the present invention.

In the following description of the present invention, same or similar reference numerals are used to designate the same or similar parts throughout embodiments to alleviate repetition of description for brevity.
(First Embodiment)

As shown in FIG. 1, an internal combustion engine 1, which is also referred to hereafter simply as an engine, is designed as a four-cylinder/four-cycle spark ignition system. Intake air from the upstream side passes through an air cleaner 2, an intake pipe 3, a throttle valve 4, a surge tank 5 and intake manifolds 6. The intake air is mixed with fuel injected from fuel injection valves 7 for each cylinder in the intake manifolds 6. The mixed gas is then supplied to the cylinders at a predetermined air-fuel ratio.

A high voltage generated by an ignition circuit 9 is distributed and supplied to ignition plugs 8 provided on each cylinder of the engine 1 by way of a distributor 10. The ignition plug 8 ignites the mixed gas in the cylinder at controlled timing. After combustion, gas exhausted from the cylinders passes through exhaust manifolds 11 and an exhaust pipe 12. At a three-way catalyst 13 provided on the exhaust pipe 12, the exhaust gas is cleaned by taking noxious components such as CO, HC and NOx from the gas. The cleaned exhaust gas is finally exhausted to the atmosphere.

On the intake pipe 3, an intake air temperature sensor 21 and an intake air pressure sensor 22 are provided. The intake air temperature sensor 21 senses an intake air temperature Tam. On the other hand, the intake air pressure sensor 22 senses an intake air pressure PM on the downstream side of the throttle valve 4. A throttle sensor 23 is linked with the throttle valve 4. Sensing a throttle opening TH, the throttle sensor 23 outputs an analog signal representing the throttle opening TH. In addition, the throttle sensor 23 also generates a detection signal when the throttle valve 4 is closed fully. On a cylinder block of the engine 1, a coolant temperature sensor 24 is provided. The coolant temperature sensor 24 senses a coolant temperature Thw in the engine 1. A rotation speed sensor 25 is provided on the distributor 10. The rotation speed sensor 25 senses an engine rotational speed Ne. The rotation speed sensor 25 outputs 24 pulses at fixed angular intervals for each two rotations of the engine 1 or for each 720 degrees CA.

In addition, on the upstream side of the three-way catalyst 13 of the exhaust pipe 12, an air-fuel ratio sensor 26 is provided. The air-fuel ratio sensor 26 is the limit current type for outputting a signal representing an air-fuel ratio (A/F or $\lambda$) over a wide range, the value of which is proportional to the oxygen concentration in the gas exhausted from the engine 1. On the downstream side of the three-way catalyst 13, an oxygen sensor 27 is provided. The oxygen sensor 27 outputs a voltage VOX2 indicating whether the air-fuel ratio is rich or lean with respect to the stoichiometric air-fuel ratio point ($\lambda=1$).

An electronic control unit (ECU) 40 is provided for controlling the operation of the engine 1. It comprises an engine control circuit 50 which controls fuel injection and ignition, and a sensor driving circuit 60 for controlling the operation to drive the air-fuel ratio sensor 26. The engine control circuit serves as a logic processing circuit comprising mainly a CPU (central processing unit) 51, a ROM (read-only memory) 52, a RAM (random-access memory) 53 and a back-up RAM 54. The engine control circuit 50 receives detection signals such as the intake air temperature Tam, the intake air pressure PM, the throttle opening TH, the coolant temperature Thw, the engine rotation speed Ne and the air-fuel ratio signals $\lambda$ and VOX2 generated by the sensors 26 and 27. Then, the engine control circuit 50 determines control signals representing quantities such as a fuel injection amount TAU and ignition timing Ig from the detection signals. These control signals are applied to the injection valve 7, the ignition circuit 9 and other components. The ECU 40 is connected to a battery 41 which serves as a main power supply. A heater 33 controlled by the ECU 40 is provided for the air-fuel ratio sensor 26 to activate and maintain the activation of the air-fuel ratio sensor 26.

Figure 2:
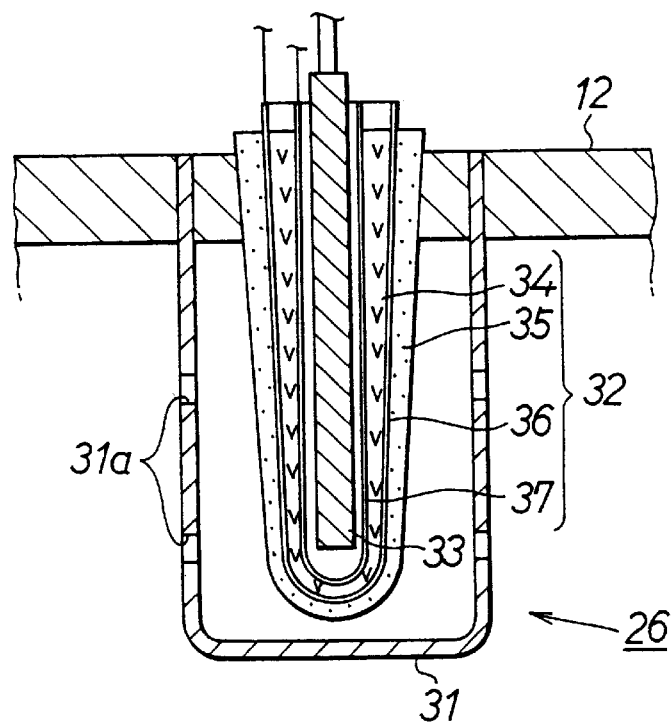
FIG. 2 is a cross-sectional view showing an air-fuel ratio sensor employed in the first embodiment.

As shown in FIG. 2, the air-fuel ratio sensor 26 provided in the exhaust pipe 12 includes a cover 31, a sensor body 32 and a heater 33. The cross section of the cover 31 has a U shape. A number of small holes 31a are drilled through the wall of the cover 31 to provide paths connecting the outside and the inside of the cover 31. The sensor body 32 outputs a limit current representing an oxygen concentration in the lean zone of the air-fuel ratio or the concentrations of unburned gases such as Co, HC and H2 in the rich zone of the air-fuel ratio.

The sensor body 32 comprises a solid electrolyte layer 34 having a cross section resembling a cup, an exhaust-side electrode layer 36, an atmosphere-side electrode layer 37 and a diffused resistor layer 35. The exhaust-side electrode layer 36 is fixed on the outer surface of the solid electrolyte layer 34 and used as a measured-gas-side electrode while the atmosphere-side electrode layer 37 is fixed on the inner surface of the solid electrolyte layer 34 and used as a reference-gas-side electrode. The diffused resistor layer 35 is provided on the outer side of the exhaust-side electrode layer 36 by using typically a plasma spraying technique. The solid electrolyte layer 34 is made of an oxygen ion conductive oxide sintered body which is solid-solved in a material such as $ZrO_2$, $HfO_2$, $ThO_2$ and $Bi_2O_3$ with a material such as CaO, MgO, $Y_2O_3$ and $Yb_2O_3$ used as a stabilizer. The diffused resistor layer 35 is made of a heat resisting inorganic material such as alumina, magnesia, silica, spinel and mullite. The exhaust-side electrode layer 36 and the atmosphere-side electrode layer 37 are both made of a noble metal with a high catalytic activity such as platinum and provided by using a porous chemical plating technique. It should be noted that the area and the thickness of the exhaust-side electrode layer 36 are in the ranges of 5 to 100 square millimeters and 0.5 to 2.0 microns respectively. On the other hand, the area and the thickness of the atmosphere-side electrode layer 37 is in the ranges greater than about 5 square millimeters and 0.5 to 2.0 microns respectively.

The heater 33 is accommodated in the atmosphere-side electrode layer 37. The thermal energy generated by the heater 33 heats the sensor body 32 which comprises the atmosphere-side electrode layer 37, solid electrolyte layer 34, exhaust-side electrode layer 36 and diffused-resistor layer 35 as described above. The heater 33 has a sufficient capacity of generating heat for activating the sensor body 32.

With predetermined voltages applied between the exhaust-side electrode layer 36 and the atmosphere-side electrode layer 37, the sensor body 32 of the air-fuel ratio sensor 26 generates a limit current varying with the oxygen concentration in a zone ($\lambda>1$) leaner in fuel than the stoichiometric air-fuel ratio point ($\lambda=1$, i.e., A/F =14.7). In this case, the limit current corresponding to the concentration of oxygen is determined by the area of the exhaust-side electrode layer 36 as well as the thickness, the porosity and the average pore diameter of the diffused resistor layer 35.

The sensor body 32 is capable of detecting the concentration of oxygen in accordance with linear characteristics thereof. Since a high temperature equal to or higher than about 650 degrees Celsius is required for activating the sensor body 32 and the activating temperature range is narrow, however, the sensor body 32 can not be controlled in the active region resulting from heating by only exhaust gas of the engine 1. For this reason, the thermal heating of the heater 33 is controlled by an ECU 40 to be described later so as to maintain the sensor body 32 at or above a predetermined activation temperature. It should be noted that, in a zone ($\lambda<1$) richer than the stoichiometric air-fuel ratio point, the concentrations of unburned gases such as carbon monoxide (CO) change substantially linearly with the air-fuel ratio and the sensor body 32 generates a limit current representing the concentrations of unburned gases such as carbon monoxide (CO).

Figure 3:
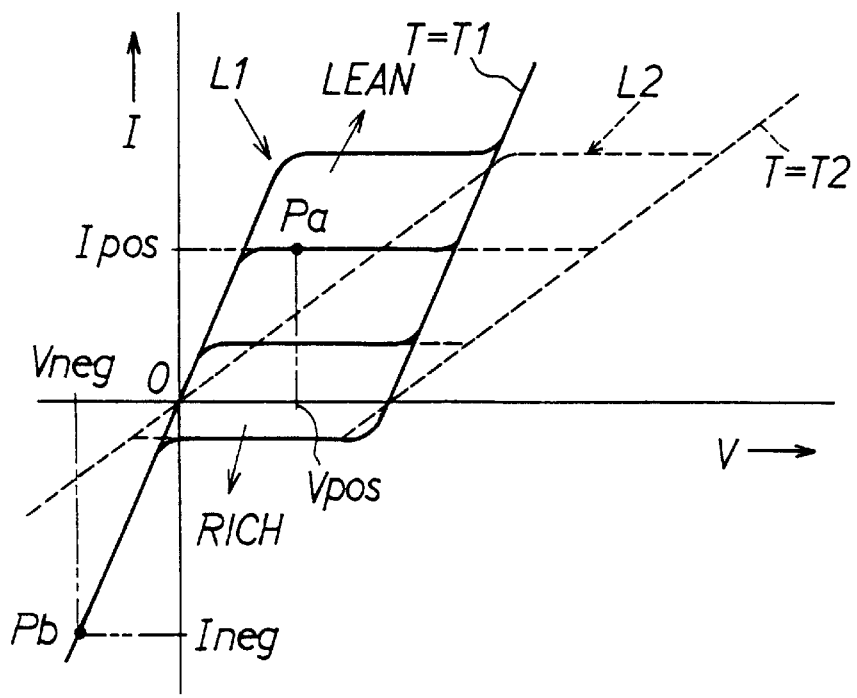
FIG. 3 is a chart showing voltage-current characteristics of the air-fuel ratio sensor shown in FIG. 2.

The above voltage-current characteristics of the sensor body 32 is shown in FIG. 3. As shown in the figure, the voltage-current (V-I) characteristics of the sensor body 32 indicates a linear relation between a current flowing through the solid electrolyte layer 34 of the sensor body 32, which is proportional to the concentration of oxygen (air-fuel ratio), and a voltage applied to the solid electrolyte layer 34. In addition, when the sensor body 32 is in an activated state at a high temperature T1 (T=T1), the state is stable as represented by a characteristics line L1 denoted by a solid line. In this case, a straight line segment of the characteristics line L1 parallel to the voltage axis V represents the limit current I of the sensor body 32 for T=T1. Increases and decreases in limit current correspond to increases and decreases in oxygen in the exhaust gas, that is, shifts to the leaner and richer zones of air-fuel ratio, respectively. The more the air-fuel ratio is shifted to the lean side, the higher the limit current becomes. The more the air-fuel ratio is shifted to the rich side, the lower the limit current becomes.

In addition, in the voltage-current characteristics, a voltage region below the straight line segment parallel to the voltage axis V is a resistance dominating region. The gradient of the characteristics line L1 min the resistance dominating region is determined by the internal resistance of the solid electrolyte layer 34 (oxygen sensing element) of the sensor body 32. The internal resistance of the solid electrolyte layer 32 of the sensor body 34 changes with temperature. To be more specific, when the temperature decreases, the internal resistance of the solid electrolyte layer 32 of the sensor body 34 increases, reducing the gradient. Thus, with the lower temperature T2 of the sensor body 32, the current-voltage characteristics are shown by a dashed line L2 in FIG. 3. In this case, a straight line segment of the characteristics line L2 parallel to the voltage axis V represents the limit current of the sensor body 32 for T=T2. As is obvious from the figure, the limit current for T=T2 is substantial equal to the limit current for T=T1 indicated by the solid line L1 for the same air-fuel ratio.

For a lean air-fuel ratio in the characteristics line L1, with a positive voltage Vpos applied to the solid electrolyte layer 34 of the sensor body 32, the current flowing through the sensor body 32 is denoted by a limit current Ipos. The relation between the positive voltage Vpos and the limit current Ipos is represented by a point Pa in FIG. 3. If a negative voltage Vneg is applied to the solid electrolyte layer 34 of the sensor body 32, the current flowing through the sensor body 32 is a negative temperature current Ineg proportional only to the temperature and independent of the concentration of oxygen or air-fuel ratio. The relation between the negative voltage Vneg and the limit current Ineg is represented by a point Pb in FIG. 3.

As described above, the air-fuel ratio sensor 26 employed in the present embodiment has linear output characteristics of the limit current dependent upon the air-fuel ratio, i.e., the concentration of oxygen in the exhaust gas. In addition, in a state with no voltages applied to the air-fuel ratio sensor 26, the air-fuel ratio sensor 26 has electromotive force characteristics which present stepwise or stepwise change (Z-form in FIG. 4) in electromotive force when the air-fuel ratio changes from a lean zone to a rich zone across the stoichiometric air-fuel ratio point ($\lambda=1$), the boundary between the lean zone and the rich zone, or vice versa. The electromotive force is generated by a difference in oxygen concentration between the atmosphere and the exhaust gas.

Figure 4:
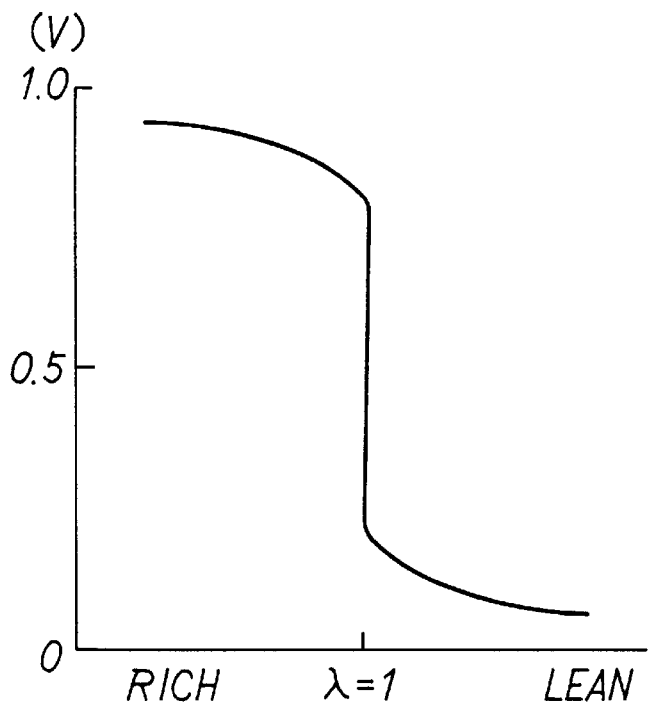
FIG. 4 is a chart showing electromotive force characteristics of the air-fuel ratio sensor.

As shown in FIG. 4, the electromotive force generated by the air-fuel ratio sensor 26 is a voltage of about 1 volt on the fuel rich zone and a voltage of about 0 volt on the fuel lean zone. The output characteristics of the electromotive force shown in FIG. 4 are about the same as the output characteristics of the downstream side oxygen sensor 27.

The sensor driving circuit 60 is shown in FIG. 5. It comprises a microcomputer 61, a bias control circuit 62 as well as an A/D converter 63 and a D/A converter 64 provided between the microcomputer 61 and the bias control circuit 62. It should be noted that the microcomputer 61 includes a CPU, a ROM and a RAM.

The microcomputer 61 outputs a current control signal Vq to a constant-current circuit 71 employed in the bias control circuit 62 by way of the D/A converter 64 in order to shift the electromotive force characteristics in the semi-activated state of the air-fuel ratio sensor 26. Specifically, the D/A converter 64 converts the current control signal vq into an analog signal output to the constant-current circuit 71 employed in the bias control circuit 62. In addition, the microcomputer 61 outputs a bias command signal Vr to the bias control circuit 62 through the D/A converter 64 in order to detect a desired air-fuel ratio in a complete activated state of the air-fuel ratio sensor 26. That is, the D/A converter 64 converts the bias command signal Vr into an analog signal Vc which is then output to the bias control circuit 62.

The bias control circuit 62 includes a reference voltage circuit 65, a first voltage supply circuit 66, a second voltage supply circuit 67, a current detecting circuit 68, and a pair of switch circuits 69 and 70 as well as the constant current circuit 71. As described above, the air-fuel ratio sensor 26 employed in the present embodiment has first characteristics which exhibit the stepwise change in electromotive force when the air-fuel ratio changes from the lean zone to the rich zone across the stoichiometric air-fuel ratio point, the boundary between the lean zone and the rich zone, or vice versa, and second linear output characteristics showing dependence of the limit current upon the air-fuel ratio. The air-fuel ratio sensor 26 is switched from the first characteristics to the second one and vice versa by switching over the operating states of the switch circuits 69 and 70.

In the state shown in FIG. 5, the switch circuits 69 and 70 are connected to contact points 69a and 70a, conductive state), respectively. In this state, the air-fuel ratio sensor 26 operates in accordance with the second characteristics (linear output characteristics). When the switches circuit 69 and 70 are switched over to contact points 69b and 70b, nonconductive state, respectively, on the other hand, the air-fuel ratio sensor 26 operates in accordance with the first characteristics (stepwise characteristics).

The reference voltage circuit 65 has a pair of potentiometer resistors 65a and 65b for generating a fixed reference voltage Va. The first voltage supply circuit 66 works as a voltage follower circuit for supplying an output voltage equal in magnitude to the fixed reference voltage Va generated by the reference voltage circuit 65 to the contact point 69a of the switch circuit 69. The first voltage supply circuit 66 comprises an operational amplifier 66a, an NPN transistor 66b and a PNP transistor 66c. The positive input terminal of the operational amplifier 66a for inputting the reference voltage Va is connected to the output point between the resistors 65a and 65b while the negative input terminal thereof is connected to the contact point 69a of the switch circuit 69. The bases of the NPN transistor 66b and the PNP transistor 66c are connected to the output terminal of the operational amplifier 66a. The collector of the NPN transistor 66b is connected to a constant voltage power supply Vcc and the emitter thereof is connected to the contact point 69a of the switch circuit 69 through a current detecting resistor 68a employed in the current detecting circuit 68.

The emitter of the PNP transistor 66c is connected to the emitter of the NPN transistor 66b and the collector of the PNP transistor 66c is connected to the ground.

In similar manner, the second voltage supply circuit 67 also works as a voltage follower circuit for supplying an output voltage equal in magnitude to the voltage signal Vc output by the D/A converter 64 to the contact point 70a of the switch circuit 70. The second voltage supply circuit 67 comprises an operational amplifier 67a, an NPN transistor 67b and a PNP transistor 67c. The positive input terminal of the operational amplifier 67a is connected to the output terminal of the D/A converter 64 for generating the voltage Vc while the negative input terminal thereof is connected to the contact point 70a of the switch circuit 70. The bases of the NPN transistor 67b and the PNP transistor 67c are connected to the output terminal of the operational amplifier 67a. The collector of the NPN transistor 67b is connected to a constant voltage power supply Vcc and the emitter thereof is connected to the contact point 70a of the switch circuit 70. The emitter of the PNP transistor 67c is connected to the emitter of the NPN transistor 67b and the collector of the PNP transistor 66c is connected to the ground.

The switch circuits 69 and 70 are connected to two terminals 73 and 74 of the air-fuel ratio sensor 26, respectively. More specifically, the terminal 73 of the air-fuel ratio sensor 26 connected to the switch circuit 69 is connected to the atmosphere-side electrode layer 37 of the air-fuel ratio sensor 26 shown in FIG. 2, while the terminal 74 of the air-fuel ratio sensor 26 connected to the switch circuit 70 is connected to the exhaust-side electrode layer 36 of the air-fuel ratio sensor 26. The switching-over operations of the switch circuits 69 and 70 are carried out simultaneously at the same time under the control of the microcomputer 61. In the state shown in FIG. 5, the switch circuits 69 and 70 are connected to the contact points 69a and 70a, respectively. Accordingly, in this state, the voltages Va and Vc generated by the first and second voltage supply circuits 66 and 67 are applied to the terminals 73 and 74 of the air-fuel ratio sensor 26, respectively.

That is to say, in the state shown in FIG. 5, the fixed reference voltage Va is supplied to the terminal 73 of the air-fuel ratio sensor 26. At that time, if the voltage Vc supplied to the other terminal 74 of the air-fuel ratio sensor 26 by way of the D/A converter 64 is lower than the reference voltage Va (Vc<Va), the air-fuel ratio sensor 26 is positively biased. If the voltage Vc supplied to the terminal 74 of the air-fuel ratio sensor 26 is higher than the reference voltage Va (Vc>Va), on the other hand, the air-fuel ratio sensor 26 is negatively biased. In either case, the magnitude of the limit current that flows due to the voltage applied between the terminals 73 and 74 of the air-fuel ratio sensor 26 is detected as a difference in voltage between both ends of the current detecting resistor 68a. The difference in voltage is supplied to the microcomputer 61 by way of the A/D converter 63.

With the switch circuits 69 and 70 connected to the contact points 69b and 70b respectively, on the other hand, the contact points 69b and 70b are connected to the air-fuel ratio sensor 26. In this state, the air-fuel ratio sensor 26 is connected in parallel with an electromotive force detecting resistor 72 for detecting the electromotive force generated by the air-fuel ratio sensor 26. The electromotive force generated by the air-fuel ratio sensor 26 detected by the electromotive force detecting resistor 72 is supplied to the microcomputer 61 by way of the A/D converter 63.

The contact points 69b and 70b of the switch circuits 69 and 70 are respectively connected to output terminals of 3 the constant current circuit 71. In this sate, the microcomputer 61 outputs the current control signal Vq to the constant current circuit 71 by way of the D/A converter 64. Receiving the current control signal Vq, the constant current circuit 71 generates a forced current flowing to the exhaust-gas-side electrode layer 36 or the atmosphere-side electrode layer 37 of the air-fuel ratio sensor 26 in order to shift the first characteristics of the air-fuel ratio sensor 26. That is, an air-fuel ratio in the first characteristics shown in FIG. 4 at which the electromotive force abruptly changes is moved to the lean side or the rich side of the air-fuel ratio from the stoichiometric air-fuel ratio point. It should be noted that a resistor 75 is provided between the constant current circuit 71 and the contact point 69b.

The first characteristics of the air-fuel ratio sensor 26 are shifted as follows. As described above, the exhaust-side electrode layer 36 and the atmosphere-side electrode layer 37 are provided on both sides of the solid electrolyte layer 34 of the air-fuel ratio sensor 26. When a forced current I flows into the atmosphere-side electrode layer 37 as shown by an arrow in FIG. 6A, oxygen ions move from the exhaust-side layer 36 to the atmosphere-side electrode layer 37 through the solid electrolyte layer 34. As a result, the amount of oxygen in the exhaust gas decreases, causing the electromotive force generated by the air-fuel ratio sensor 26 to abruptly change at the air-fuel ratio in a zone leaner than the stoichiometric air-fuel ratio point ($\lambda=1$) as shown by a solid line in FIG. 6B. That is, the electromotive force characteristics (first characteristics) of the air-fuel ratio sensor 26 are shifted to the lean side.

Figure 6B:
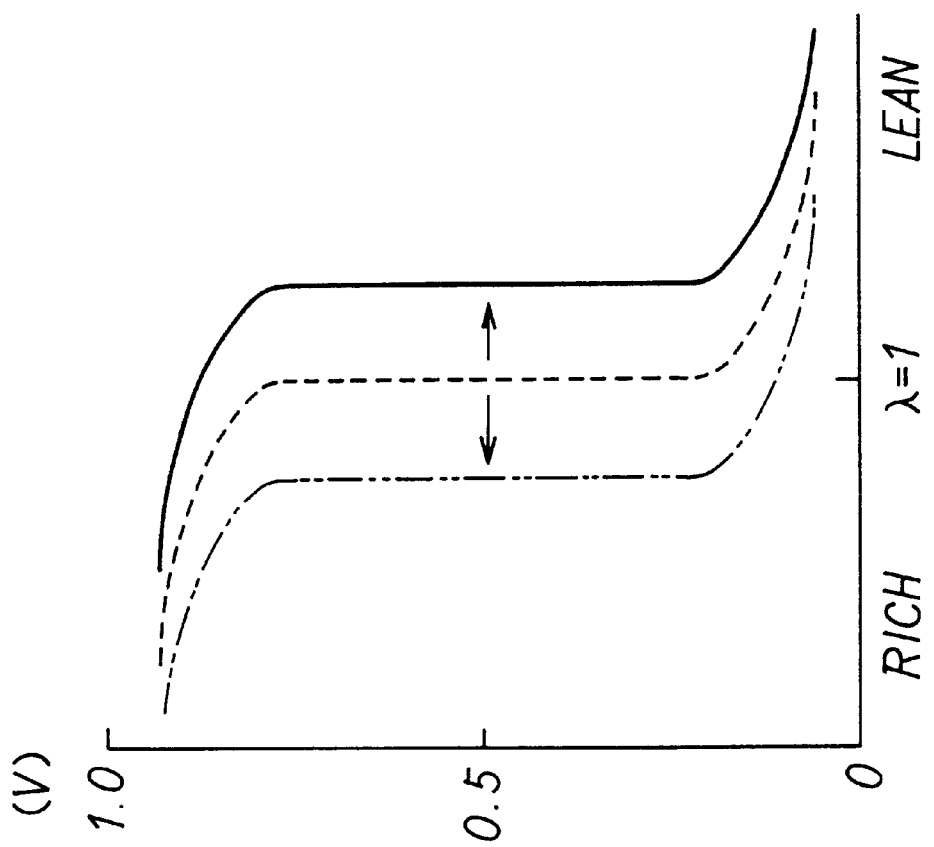
FIGS. 6A and 6B are a schematic view of the sensor and a chart showing shift of electromotive force characteristics of the air-fuel ratio sensor, respectively.
Figure 6A:
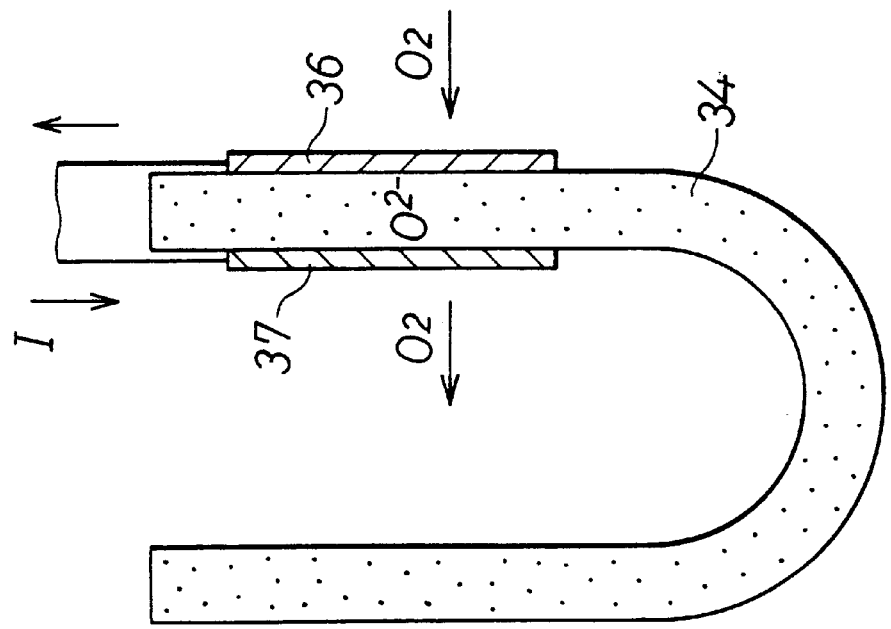

When a forced current flows into the exhaust-side electrode layer 36 in a direction opposite to the arrow shown in FIG. 6A, on the other hand, oxygen ions conversely move from the atmosphere-side layer 37 to the exhaust-side electrode layer 36 through the solid electrolyte layer 34. As a result, the amount of oxygen in the exhaust gas increases, causing the electromotive force generated by the air-fuel ratio sensor 26 to abruptly change at an air-fuel ratio in a zone richer than the stoichiometric air-fuel ratio point ($\lambda=1$)

as shown by a two-dot chain line in FIG. 6B. That is, the electromotive force characteristics (the first characteristics) of the air-fuel ratio sensor 26 are shifted to the rich side.

Figure 7:
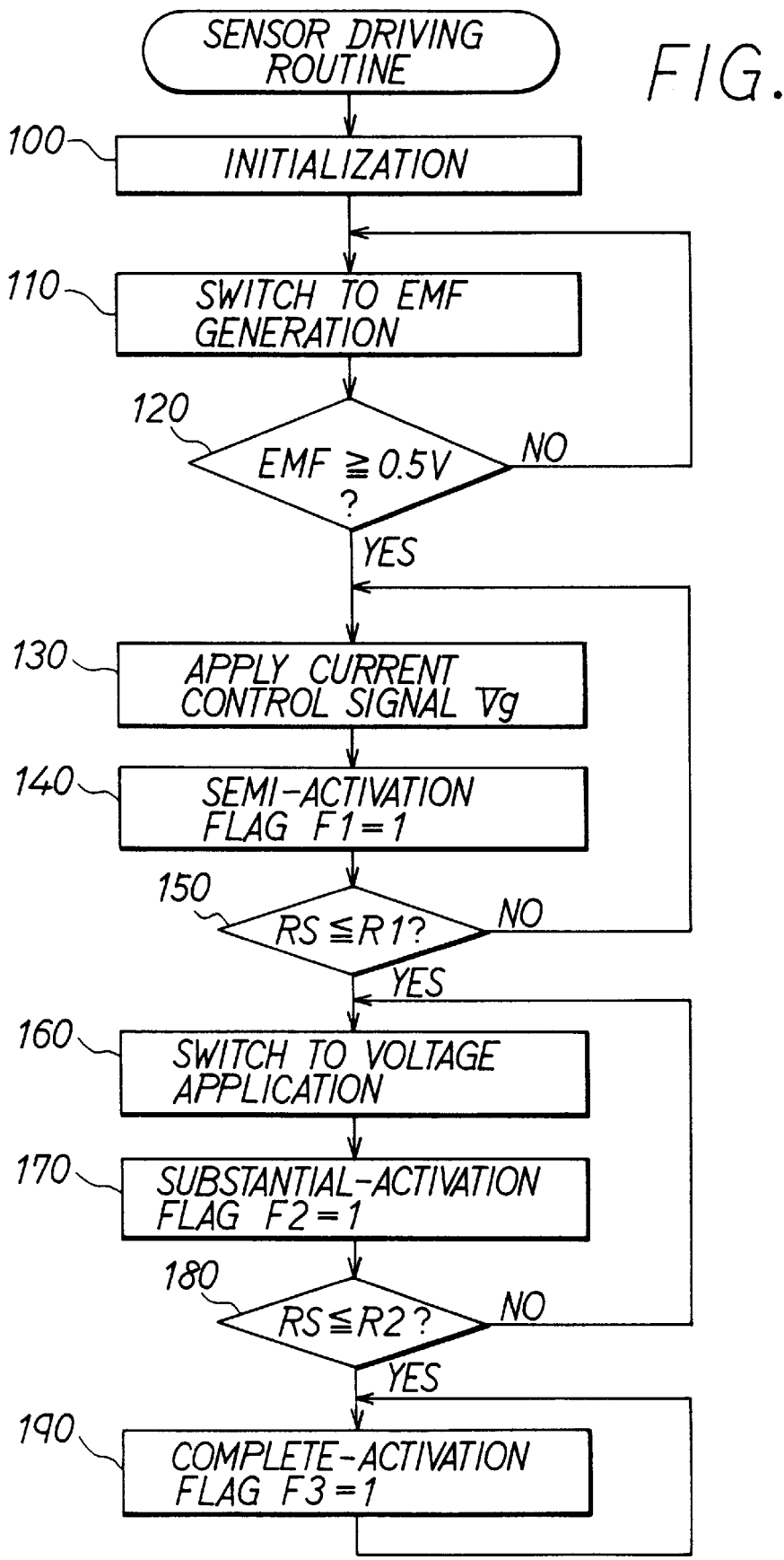
FIG. 7 is a flowchart of a sensor driving routine executed by the sensor driving unit shown in FIG. 5.

The above-described shift in the output of the air-fuel ratio sensor 26 is controlled by the microcomputer 61 in the sensor driving unit 60 according to the process defined by a flowchart shown in FIG. 7. This routine starts at the power-on time of the ECU 40, i.e., the sensor driving circuit 60.

The routine starts with a step 100 at which the microcomputer 61 carries out initialization processing. In the initialization processing, the microcomputer 61 clears, among other things, activation flags F1, F2 and F3 representing the activation states of the air-fuel ratio sensor 26. The activation flags F1, F2 and F3 are used to represent the activation state at three different stages in a process to put the air-fuel ratio sensor 26 in a complete activated state in which an accurate limit current can be output. More specifically, F1 is an activation flag which is set to "1" to indicate that the air-fuel ratio sensor 26 is in a semi-activated state. F1 is referred to hereafter as a semi-activation flag. On the other hand, F2 is an activation flag which is set to "1" to indicate that the air-fuel ratio sensor 26 in a substantially activated state prior to a complete activated state. F2 is referred to hereafter as an substantial activation flag. Finally, F3 is an activation flag which is set to "1" to indicate that the air-fuel ratio sensor 26 is in a completely activated state. F3 is referred to hereafter as a complete activation flag.

The processing then moves to a step 110 at which the microcomputer 61 puts the switch circuits 69 and 70 in the sensor driving circuit 60 shown in FIG. 5 in an electromotive force generating state, a state causing the air-fuel ratio sensor 26 to generate an electromotive force (EMF). The terminals 73 and 74 of the air-fuel ratio sensor 26 are connected to the contact points 69b and 70b of the switch circuits 69 and 70, respectively, reversing the connection in a state opposite to the state shown in FIG. 5. In such a state, the air-fuel ratio sensor 26 is disconnected from the first and second voltage supply circuits 66 and 67, generating an electromotive force corresponding to the concentration of oxygen in the exhaust gas. The electromotive force is detected by the electromotive force detecting resistor 72.

The processing then proceeds to a step 120 at which the microcomputer 61 determines whether the electromotive force generated by the air-fuel ratio sensor 26 is equal to or greater than a value of typically 0.5 volt. If the electromotive force is equal to or greater than 0.5 volt, the microcomputer 61 determines that the air-fuel ratio sensor 26 has been activated to a state at which the electromotive force generated thereby can be used in feedback control of the air-fuel ratio. In this case, the processing continues to a step 130. Otherwise, the processing returns to the step 110.

At the step 130, the microcomputer 61 outputs the current control signal Vq to the constant current circuit 71 shown in FIG. 5 through the D/A converter 64 in order to shift the electromotive force characteristics of the air-fuel ratio sensor 26, that is, to shift an air-fuel ratio point in the first characteristics at which the electromotive force abruptly changes to the lean side or the rich side from the stoichiometric air-fuel ratio point. At the step 130, the constant current circuit 71 supplies a forced current into the atmosphere-side electrode layer 37 or the exhaust-side electrode layer 36 of the air-fuel ratio sensor 26 so that an air-fuel ratio point in the first characteristics at which the electromotive force abruptly changes is shifted to the lean side or the rich side of the air-fuel ratio from the stoichiometric air-fuel ratio point as shown in FIG. 6B. The air-fuel ratio point in the first characteristics at which the electromotive force stepwise changes is determined arbitrarily by the specifications and characteristics of the individual engine. In order to reduce the amount of the HC component right after the starting of the engine, the air-fuel ratio point is set on the lean side as shown by the solid line in FIG. 6B. In the present embodiment, the output characteristics shifted to the lean side are used to detect the electromotive force.

The processing then moves on to a step 140 at which the microcomputer 61 sets the semi-activation flag F1 to "1". Subsequently, the processing proceeds to a step 150 at which the microcomputer 61 determines whether a sensing element resistance RS, that is, the internal impedance (resistance) of the solid electrolyte layer 34, is equal to or smaller than a first criterion value R1 for determining the activation state of the air-fuel ratio sensor 26. If the determination at the step 150 is NO, the flow of processing returns to the step 130 to repeat the steps 130 through 150 till the determination at the step 150 becomes YES, that is, till the sensing element resistance RS becomes equal to or smaller than the first criterion resistance R1.

Figure 8:
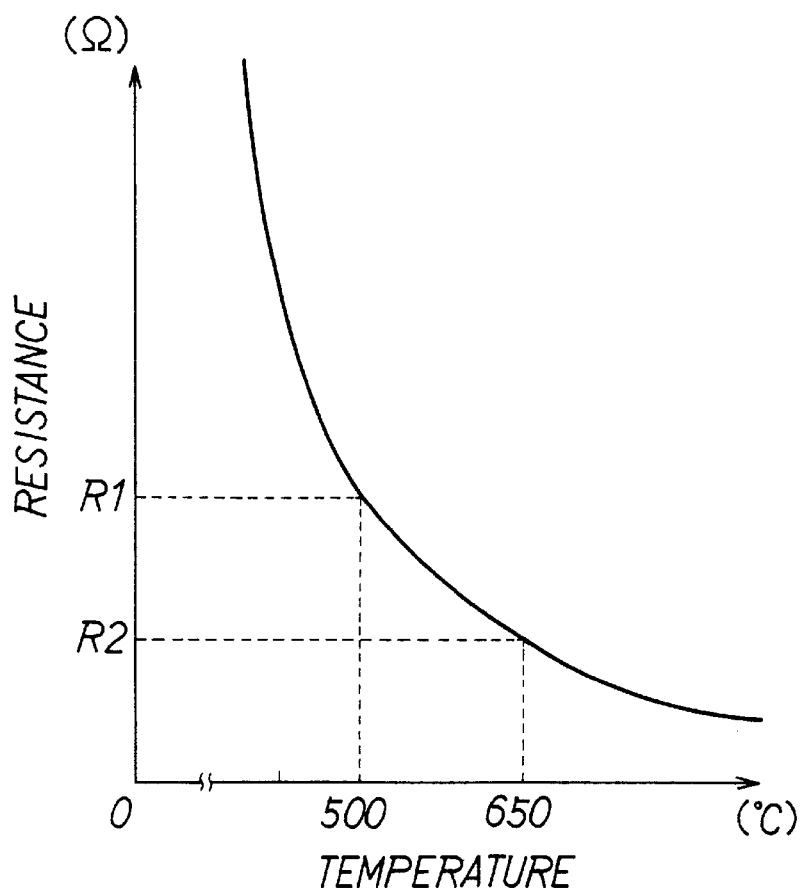
FIG. 8 is a chart showing a relation between the sensing element temperature and the sensing element resistance of the air-fuel ratio sensor.

The sensing element resistance RS may be determined by another resistance detecting routine which is not shown in the figure. That is, the sensing element resistance RS may be computed from a voltage applied to the air-fuel ratio sensor 26 and a current output by the air-fuel ratio sensor 26 (resistance=applied voltage/output current). The first criterion value R1 is set to correspond to a resistance RS which will exist at a temperature of about 500 degrees Celsius as shown in FIG. 8. The value R1 is a criterion value for determining whether the air-fuel ratio sensor 26 is in a state of being capable of outputting a limit current only in a portion of the air-fuel ratio zone, that is, a substantial or almost activated state. It should be noted that FIG. 8 shows characteristics that, the higher the temperature of the sensing element, the lower the resistance RS of the sensing element.

As the activation of the air-fuel ratio sensor 26 progresses, the sensing element resistor RS becomes smaller than the first criterion value R1, making the determination at the step 150 YES. In this case the processing moves on to a step 160 at which the microcomputer 61 switches the switch circuits 69 and 70 in a state of applying voltages to the air-fuel ratio sensor 26. The contact points 69a and 70a of the switch circuits 69 and 70 are switched to a state of being connected to the terminals 73 and 74 of the air-fuel ratio sensor 26 respectively as shown in FIG. 5. In this state, the voltages generated by the first and second voltage supply circuits 66 and 67 are applied to the air-fuel ratio sensor 26, causing the air-fuel ratio sensor 26 to generate a limit current with the magnitude which corresponds to the concentration of oxygen in the exhaust gas.

The flow of processing then continues to a step 170 at which the microcomputer 61 sets the substantial activation flag F2 to "1". Subsequently, the processing proceeds to a step 180 at which the microcomputer 61 determines whether the sensing element resistance RS is equal to or smaller than a second criterion value R2. The second criterion value R2 is the value of the resistance RS which will exist at a temperature of about 650 degrees Celsius as shown in FIG. 8. The value R2, a value smaller than R1, is a criterion value for determining whether the air-fuel ratio sensor 26 is in a complete activated state. It should be noted that, when the F2 is set to "1", the semi-activation flag F1 is cleared to "0".

If the sensing element resistance RS is greater than the second criterion value R2, the processing returns to the step S160 to repeat the steps 160 through 180 till the determination at the step 180 becomes YES. As the resistance RS is equal to or smaller than the second criterion value R2, the processing moves on to a step 190 at which the microprocessor 61 sets the complete activation flag F3 to "1". Thereafter, the bias control circuit 62 of the sensor driving circuit 60 is kept at a state of applying the voltages to the air-fuel ratio sensor 26 and the complete activation flag F3 remains set to "1". It should be noted that, when the complete activation flag F3 is set to "1", the flag F2 is cleared to "0".

Figure 9:
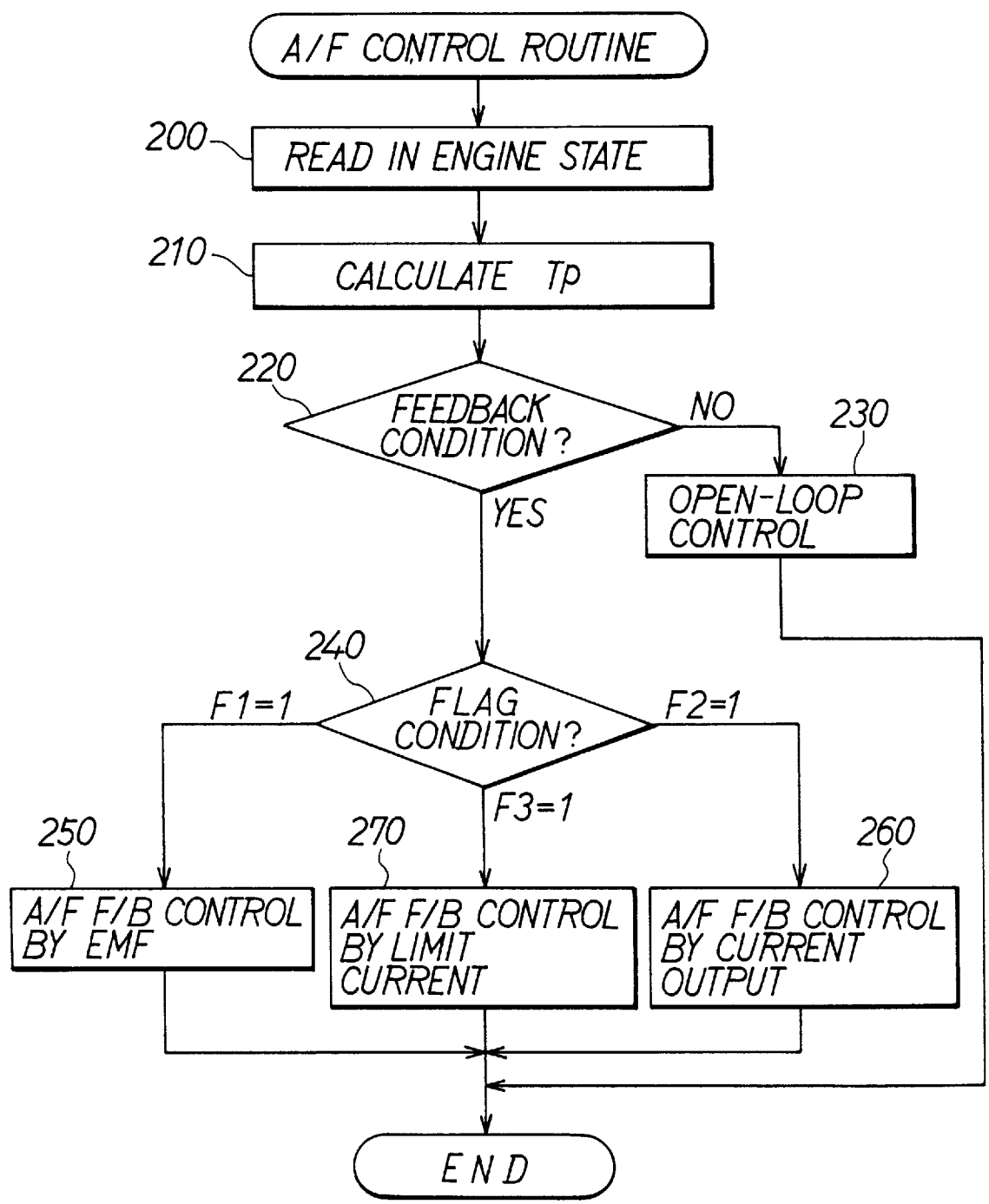
FIG. 9 is a flowchart of an air-fuel ratio control routine executed by a CPU employed in the first embodiment.

An air-fuel ratio control routine is shown in FIG. 9. This routine is executed by the CPU 51 in the engine control circuit 50 for each fuel injection, that is, for every 180 degrees CA in the case of the present embodiment.

The routine starts with a step 200 at which the CPU 51 reads in detection results showing the operating state of the engine such as the rotation speed Ne, the intake air pressure PM and the coolant temperature Thw from the various sensors. The processing then moves on to a step 210 at which a basic injection quantity Tp from the rotation speed Ne of the engine and the intake air pressure PM is computed by using a basic injection map stored in the ROM 52. The processing then proceeds to a step 220 at which the CPU 51 determines whether the air-fuel ratio feedback conditions are satisfied. The air-fuel ratio feedback conditions include that the coolant temperature Thw is higher than a predetermined value and the engine is not in a high speed and heavy load state. The air-fuel ratio feedback conditions also include that the air-fuel ratio sensor 26 is in the activated state to a certain degree, that is, the electromotive force generated by the air-fuel ratio sensor 26 is equal to or greater than 0.5 V as determined in the step 120 of the flowchart shown in FIG. 7. This activation condition can also be determined using a flag.

If the air-fuel ratio feedback conditions are not satisfied (NO), the processing continues to a step 230 at which the CPU 51 implements the open-loop air-fuel ratio control, ending this routine. The basic injection quantity Tp is increased by adding variances compensating for low temperature and heavy load corrections to determine a final fuel injection amount TAU as a result of the corrections. Then, fuel injection control based on the final fuel injection amount TAU is carried out by means of the fuel injection valve 7. At that time, a feedback correction coefficient FAF is kept at 1.

If the air-fuel ratio feedback conditions are satisfied (YES) at the step 220, on the other hand, the processing continues to a step 240 at which the CPU 51 reads out the activation flags F1, F2 and F3 of the air-fuel ratio sensor 26 set by the routine shown in FIG. 7 to determine the flag condition, i.e., if any of the flags is set to "1". In the case that the engine has been started, the semi-activated flag F1 may have been set to "1". In this case, the processing moves on to a step 250 at which the CPU 51 implements feedback control of the air-fuel ratio based on the electromotive force generated by the air-fuel ratio sensor 26. After the processing carried out at the step 250 is completed, the routine is terminated.

In this case, the air-fuel ratio sensor 26 has characteristics in which the electromotive force changes abruptly at an air-fuel ratio shifted from the stoichiometric air-fuel ratio point to the lean or rich zone to a certain degree. The CPU 51 implements the feedback control with an air-fuel ratio point in the lean or rich zone used as a target air-fuel ratio. As an example, it is assumed that the target air-fuel ratio is in the lean zone in the present embodiment. Such a target ratio is referred to as a lean target air-fuel ratio. If the air-fuel ratio detected by the air-fuel ratio sensor 26 is located more in a zone even leaner than the lean target air-fuel ratio, the feedback correction coefficient FAF is increased in order to raise the fuel injection amount TAU. It should be noted that TAU=Tp×FAF+$\alpha$ where $\alpha$ is a correction value. If the air-fuel ratio detected by the air-fuel ratio sensor 26 is located in a zone richer than the lean target air-fuel ratio, the feedback correction coefficient FAF is decreased in order to reduce the fuel injection amount TAU.

If the substantial activation flag F2 is "1" at the step 240, the processing moves on to a step 260 at which the CPU 51 implements feedback control of the air-fuel ratio based on the current output of the air-fuel ratio sensor 26. If the complete activation flag F3 is "1" at the step 240, on the other hand, the processing moves on to a step 270 at which the CPU 51 implements feedback control of the air-fuel ratio based on the limit current output of the air-fuel ratio sensor 26. After finishing the processing carried out at the step 260 or 270, the present routine is ended. It should be noted that the feedback control of the air-fuel ratio implemented at the step 260 or 270 is based on the advanced control theory and explained briefly as follows.

Figure 10B:
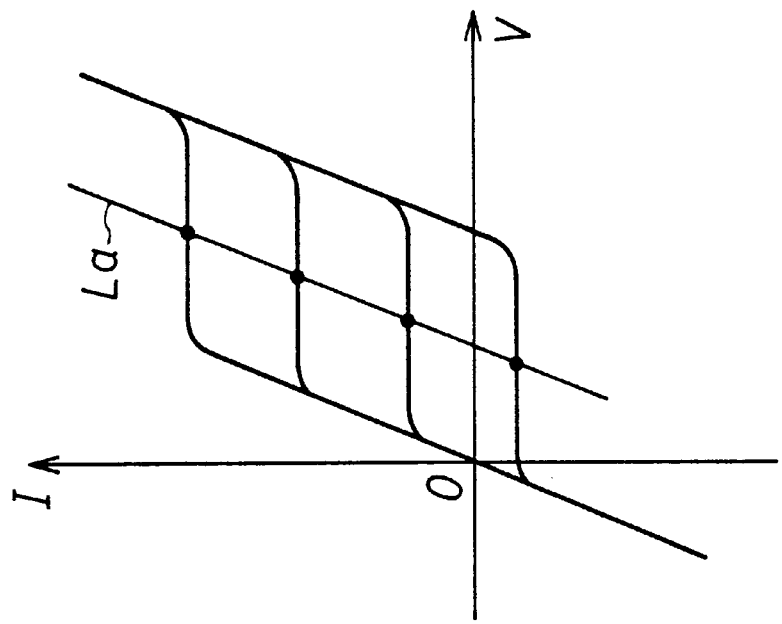
FIGS. 10A and 10B are charts each showing voltage-current characteristics of the air-fuel ratio sensor in a semi activated state and a complete activated state, respectively.
Figure 10A:
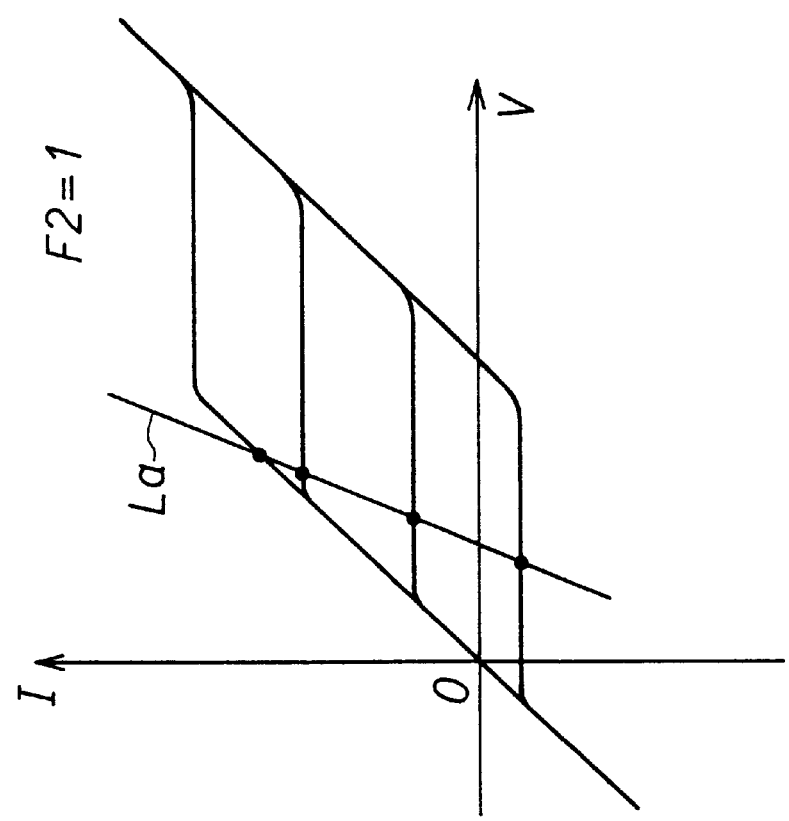

F2=1 indicates that the air-fuel ratio sensor 26 is in a substantially activated state, a state right before complete activation so that the detection accuracy at some air-fuel ratio regions deteriorates to a certain degree. On the other hand, F3=1 indicates that the air-fuel ratio sensor 26 is in a state of being completely activated so that a high detection accuracy can be obtained in all air-fuel ratio regions. The voltage-current characteristics of the air-fuel ratio sensor 26 at the time of F2=1 is shown in FIG. 10A, while the voltage-current characteristics of the air-fuel ratio sensor 26 at the time of F3=1 are shown in FIG. 10B. A straight line La shown in the figures represents applied voltage characteristics for detecting an air-fuel ratio. This applied voltage is determined by the bias command signal Vr output by the microcomputer 61 shown in FIG. 5.

That is, when the feedback control of the air-fuel ratio based on the advanced control theory is implemented, the feedback correction coefficient FAF for controlling the actual air-fuel ratio of the air-fuel ratio sensor 26 to the target air-fuel ratio is calculated by using equations (1) and (2) as follows.

$$\text{FAF}(i) = K1 \times \lambda(i) + K2 \times \text{FAF}(i-3) + K3 \times \text{FAF}(i-2) + K4 \times \text{FAF}(i-1) + \text{ZI}(i) \quad (1)$$

$$\text{ZI}(i) = \text{ZI}(i-1) - Ka \times (\lambda\text{TG} - \lambda(i)) \quad (2)$$

where $\lambda$ and $\lambda$TG represent an air-fuel ratio at an arbitrary time and the target air-fuel ratio, respectively, (i) denotes the number of times the control has been repeated since the sampling start, and K1 to K4 denote optimum feedback gains. Further, ZI(i) denotes an integration term and Ka denotes an integration constant.

Then, the final fuel injection amount TAU is computed by using the feedback correction coefficient FAF calculated as above and the basic injection amount Tp determined in accordance with the equation TAU=Tp×FAF+$\alpha$. It should be noted that the determination of the target air-fuel ratio $\lambda$TG in the equation (2) is based on the output voltage VOX2 of the downstream oxygen sensor 27. The process of determining the target air-fuel ratio $\lambda$TG is generally defined as a sub-feedback control. To be in more detail, an actual air-fuel ratio at that time is determined from the output voltage VOX2 of the downstream oxygen sensor 27. Then, it is determined whether the present actual air-fuel ratio is shifted from the target air-fuel ratio $\lambda$TG (typically from the stoichiometric air-fuel ratio point) into the lean or rich zone. If the present actual air-fuel ratio is determined to be shifted into the rich zone, the target air-fuel ratio $\lambda$TG is moved to the lean zone. If the present actual air-fuel ratio is determined to be shifted into the lean zone, on the other hand, the target air-fuel ratio λTG is moved to the rich zone.

Figure 11:
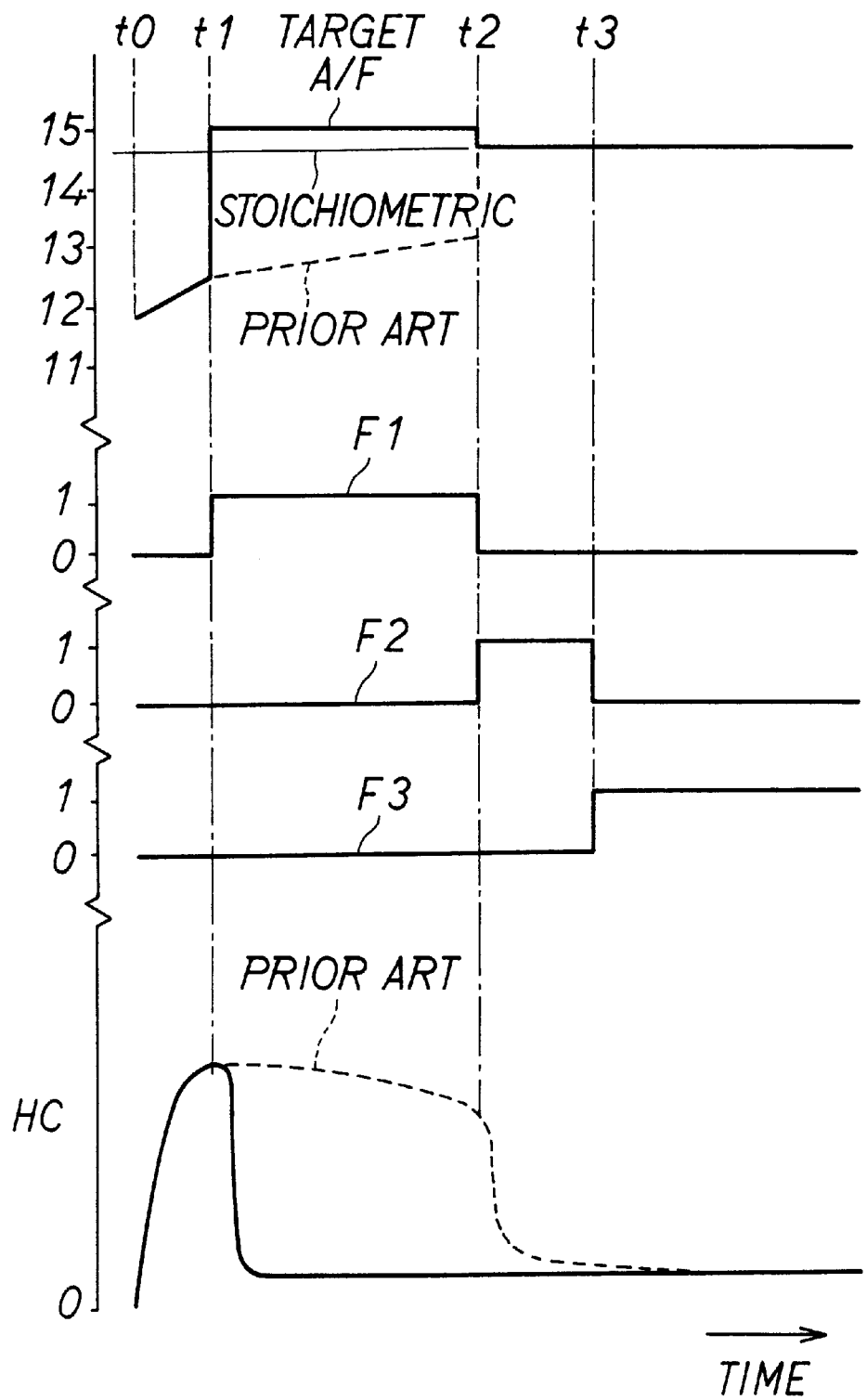
FIG. 11 is a time chart showing operations of feedback control in the first embodiment.

The present embodiment operates as shown in FIG. 11 which shows shifts of the air-fuel ratio and changes in amount of exhausted HC occurring since the start of the engine.

It is assumed that a time t0, the engine is started. At a time t1, the semi-activation flag F1 is set to "1". At a period between the time t1 and a time t2, the air-fuel ratio sensor 26 has characteristics showing a stepwise change in electromotive force at an air-fuel ratio on a side leaner than the stoichiometric air-fuel ratio point. As a result, the air-fuel ratio remains on the lean side. At the time t2, the semi-activation flag F1 is reset to "0" while the substantial activation flag F2 is set to "1". Later on, at a time t3, the substantial activation flag F2 is reset to "0" while the complete activation flag F3 is set to "1".

In the semi-activation state of the air-fuel ratio sensor 26, although the air-fuel ratio has been controlled conventionally as shown by a dashed line in the figure, it is controlled according to the present embodiment as shown by a solid line. In the case of the present embodiment, the amount of exhausted HC is much less and also decreases earlier. This is because, in the case of the conventional technology, during a period up to the start of the feedback control, that is, during a period up to the time t2, open-loop control is implemented on the rich side, causing a large amount of HC to be exhausted by the open-loop control. By starting the feedback control earlier as is the case with the present embodiment, on the other hand, the amount of exhausted HC is reduced.

The present embodiment has the following advantages.
(a) In the present embodiment, the activation state of the air-fuel ratio sensor 26 is determined. If the determination indicates that the air-fuel ratio sensor 26 is in a semi-activated state, the air-fuel ratio sensor 26 is held in a state of generating an electromotive force by not applying any voltage thereto and, at the same time, a forced current from an external source is flowed from one of a pair of electrodes of the air-fuel ratio sensor 26 to the other electrode so that the electromotive force characteristics of the air-fuel ratio sensor 26 are changed to characteristics that exhibit a stepwise change in electromotive force at an air-fuel ratio point in a zone leaner than the stoichiometric air-fuel ratio point. Then, feedback control based on the changed characteristics (electromotive force characteristics on the lean side in the case of the present embodiment) is carried out on the air-fuel ratio. In a state in which the air-fuel ratio sensor 26 is completely activated or an almost activated state right before the complete activation, feedback control using the advanced control theory based on the linear characteristics of the air-fuel ratio sensor 26 is carried out on the air-fuel ratio.

According to the present embodiment, during a period right after the start of the engine 1 up to the complete activation of the air-fuel ratio sensor 26, the feedback control can be carried out on the air-fuel ratio at a desired air-fuel ratio point which is set in accordance with the characteristics and specifications of the engine 1 even in a semi-activated state before the air-fuel ratio sensor 26 is activated. As a result, the desired control of the air-fuel ratio can be started at the earliest possible time, at the same time, it is possible to reduce noxious gas emission and maintain a good drivability.
(b) In order to shift the electromotive force characteristics of the air-fuel ratio sensor 26 to the lean or rich zone, a forced current generated by an external source is flowed to either of the exhaust-side electrode layer 36 and the atmosphere-side electrode layer 37. In this way, the characteristics representing the relation between the electromotive force and the air-fuel ratio can be shifted with ease over a relatively wide range. In the case of the stoichiometric air-fuel ratio point of 14.7, the characteristics can be shifted over an air-fuel ratio range of ±3.
(c) In addition, the activation state of the air-fuel ratio sensor 26 is determined from the level of the electromotive force of the air-fuel ratio sensor 26 at the start of the engine and the sensing element resistance RS of the air-fuel ratio sensor 26. According to this, the activation state of the air-fuel ratio sensor 26 can be determined with ease and with a high degree of reliability.

(Second Embodiment)

Figure 12:
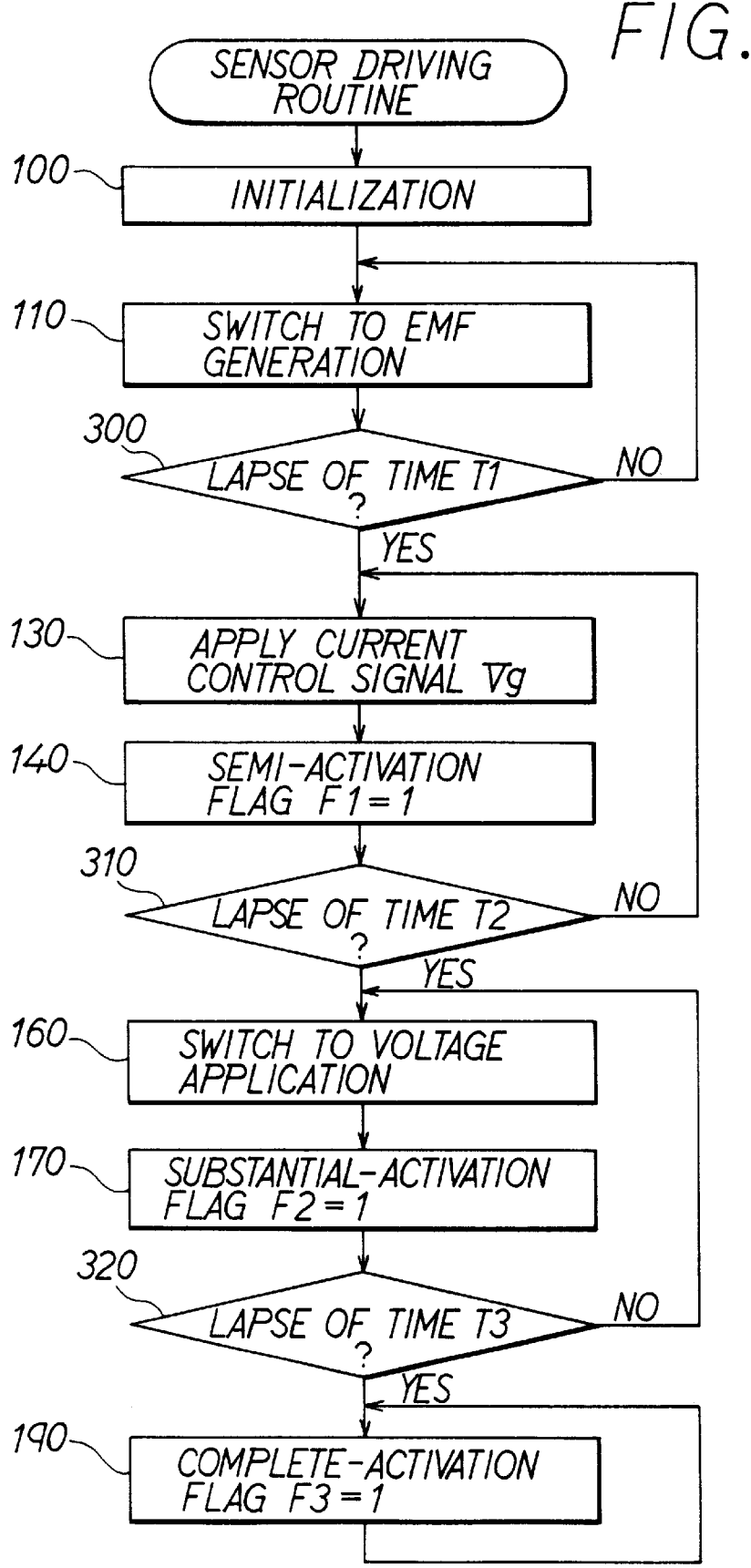
FIG. 12 a flowchart of a sensor driving routine executed in a second embodiment.

In the second embodiment shown in FIG. 12, the sensor driving routine in the first embodiment is modified in the processing to determine the activation state of the air-fuel ratio sensor 26. That is, the steps 120, 150 and 180 shown in FIG. 7 are replaced by steps 300, 310 and 320, respectively.

In the case of the second embodiment, the activation state of the air-fuel ratio sensor 26 is determined from the lapse of time since the start of the engine. At the step 300 in FIG. 12, the microcomputer 61 determines whether the time lapsing since the start of the engine has exceeded a predetermined time T1. If the determination at the step 300 is YES, the air-fuel ratio sensor 26 is determined by the microcomputer 61 as in a semi-activated state. In this case, the processing moves on to the step 130. At the step 310, the microcomputer 61 determines whether the time lapsing since the start of the engine has exceeded a predetermined time T2 (T2>T1). If the determination at the step 310 is YES, the air-fuel ratio sensor 26 is determined by the microcomputer 61 as in the substantially activated state. In this case, the processing moves on to the step 160.

Further, at the step 320, the microcomputer 61 determines whether the time lapsing since the start of the engine has exceeded a predetermined time T3 (T3>T2). If the determination at the step 320 is YES, air-fuel ratio sensor 26 is determined as in a completely activated state. In this case, the processing moves on to the step 190. It should be noted that the values of the predetermined times T1, T2 and T3 depend on whether or not the engine 1 is cold-started. The values of the predetermined times T1, T2 and T3 may be in ranges from 0 to 10 seconds, from 0 to 20 seconds and from 0 to 30 seconds, respectively. In the case of a cold start of the engine 1, the predetermined times T1, T2 and T3 are set at the upper limits of the ranges, i.e., 10 seconds, 20 seconds and 30 seconds, respectively. If the engine is re-started after completion of the warming-up, on the other hand, the predetermined times T1, T2 and T3 are all set to 0 second.

(Third Embodiment)

Figure 13:
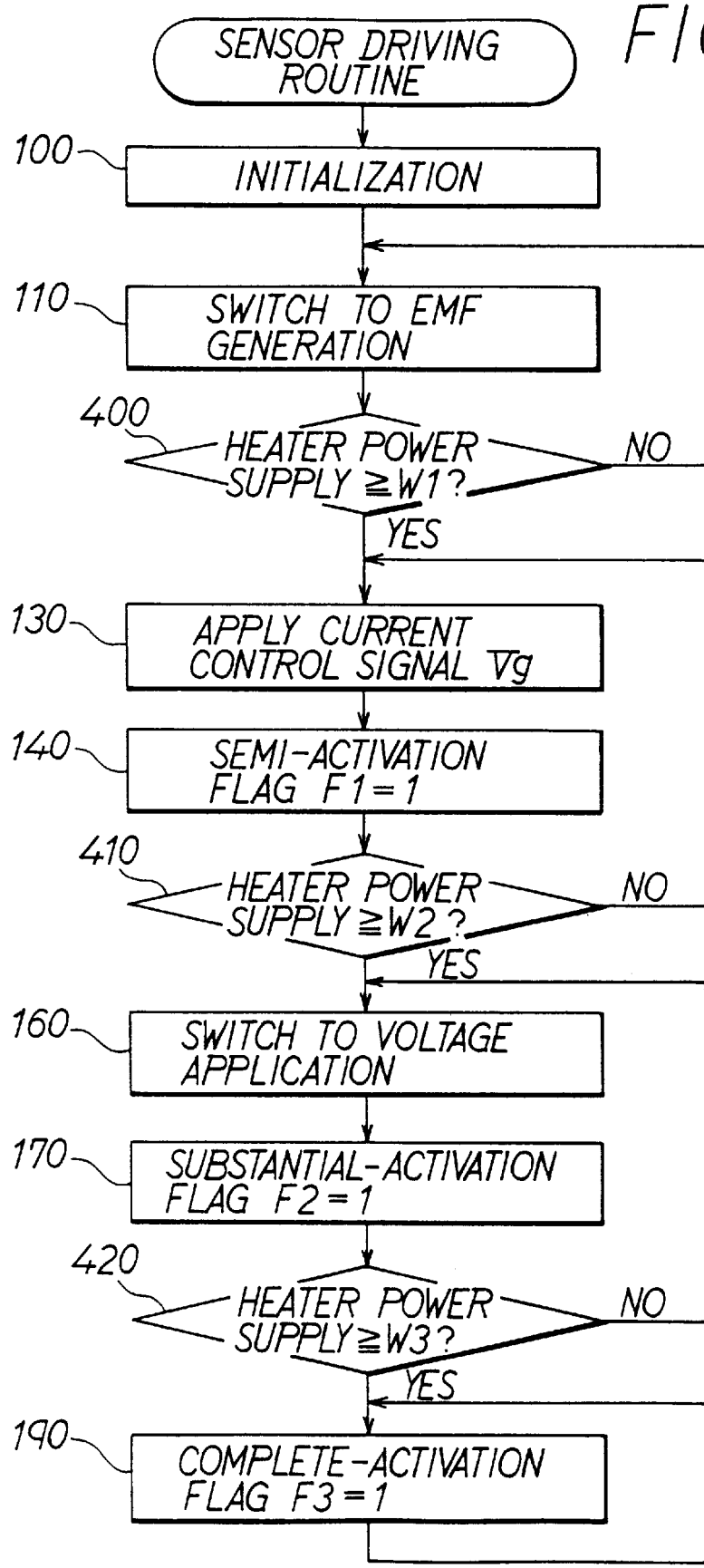
FIG. 13 a flowchart of a sensor driving routine executed in a third embodiment.

The third embodiment is a modification of the first and second embodiments in respect of determining the activation state of the air-fuel ratio sensor 26 so that the activation state of the air-fuel ratio sensor 26 is determined at steps 400, 410 and 420 from the amount of electric power supplied to the heater 33 since the start of the engine. At the step 400 in FIG. 13, the microcomputer 61 determines whether the amount of electric power supplied since the start of the engine has exceeded a predetermined quantity W1. If the determination at the step 400 is YES, the air-fuel ratio sensor 26 is determined by the microcomputer 61 as in a semi-activated state. In this case, the processing moves on to the step 140. At the step 410, on the other hand, the microcomputer 61 determines whether the amount of electric power supplied since the start of the engine has exceeded a predetermined quantity W2. If the determination at the step 410 is YES, the air-fuel ratio sensor 26 is determined by the microcomputer 61 as in the substantially activated state. In this case, the processing moves on to the step 160.

Further, at the step 420, the microcomputer 61 determines whether the amount of electric power supplied since the start of the engine has exceeded a predetermined quantity W3. If the determination at the step 420 is YES, the air-fuel ratio sensor 26 is determined by the microcomputer 61 as in a completely activated state. In this case, the processing moves on to the step 190. It should be noted that the predetermined values W1, W2 and W3 satisfy the relation W1≦W2≦W3 and depend on whether the engine 1 is cold-started. The values of the predetermined quantities W1, W2 and W3 are, in the case of a cold start of the engine 1, set at maximum values. If the engine is re-started after completion of the warming-up, on the other hand, the predetermined values W1, W2 and W3 all may be set at 0.

(Fourth Embodiment)

Figure 14:
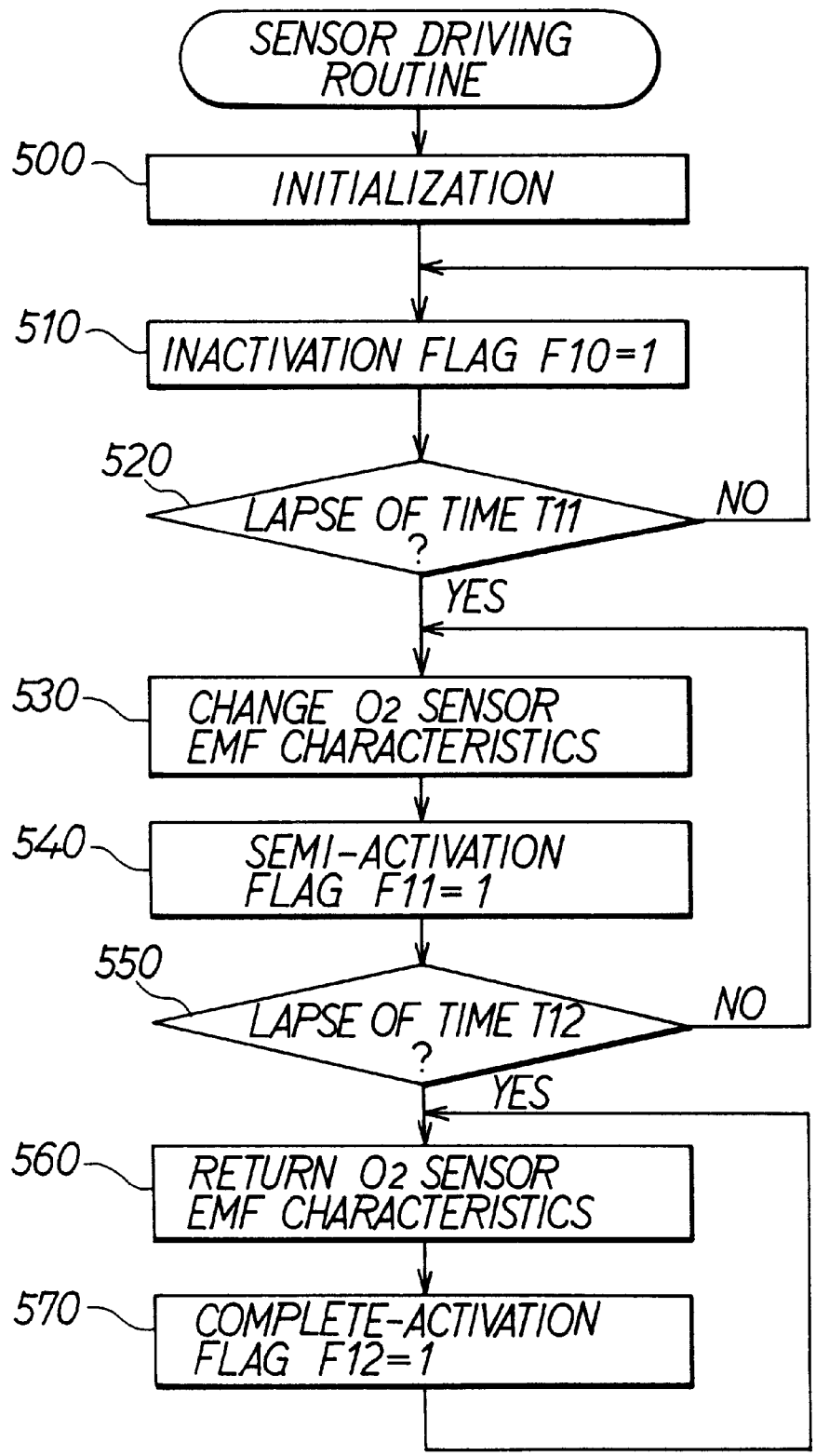
FIG. 14 a flowchart of a sensor driving routine executed in a fourth embodiment.
Figure 15:
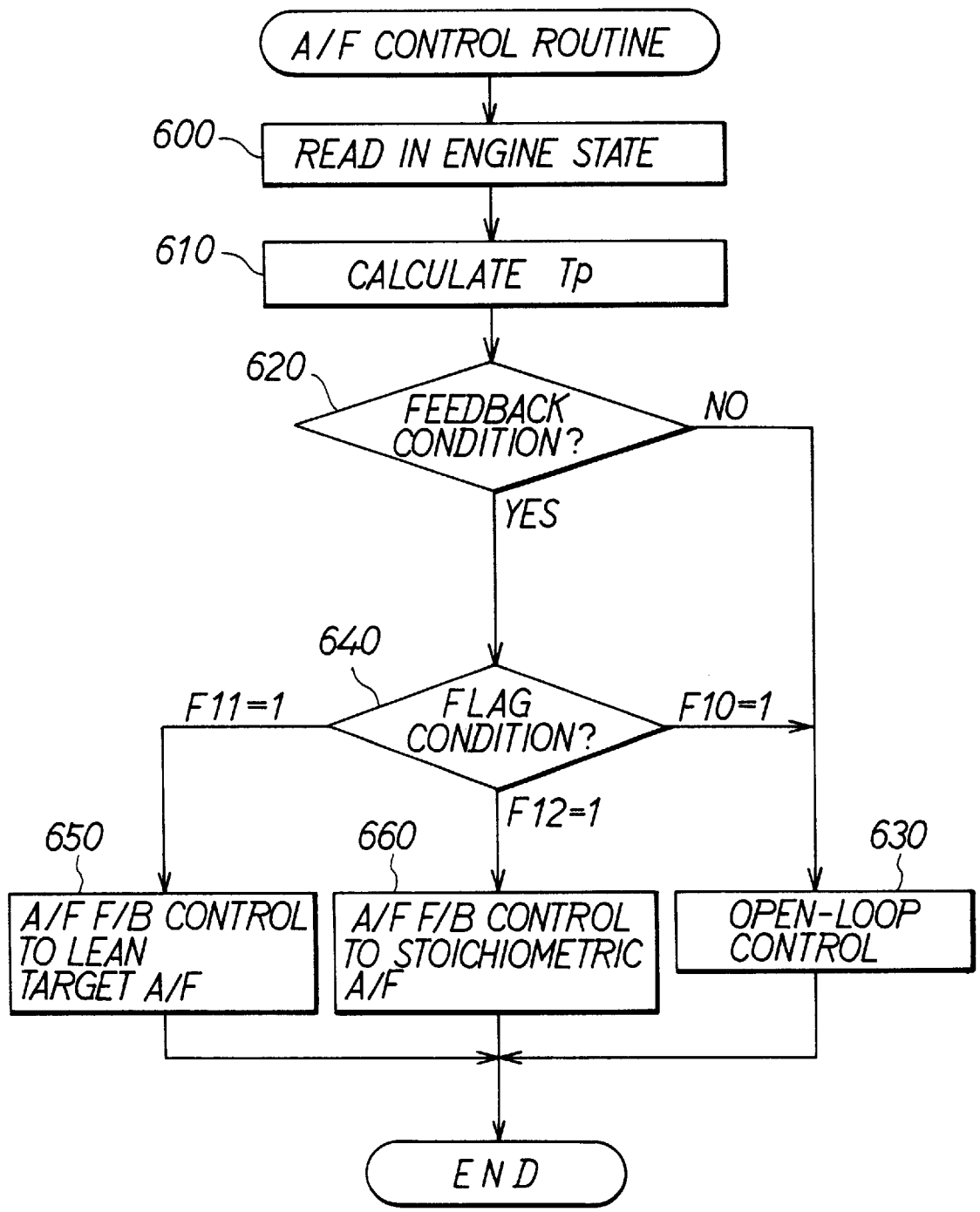
FIG. 15 a flowchart of an air-fuel ratio control routine executed in the fourth embodiment.

In the fourth embodiment shown in FIGS. 14 and 15, contrary to the first to third embodiments described above, an oxygen sensor of the electromotive force generating type is provided at the upstream of the catalyst 13 (FIG. 1) in place of the air-fuel ratio sensor 26. It should be noted that, as known in the art, the oxygen sensor comprises a solid electrolyte layer having a cross section resembling a cup for conducting oxygen ions, an exhaust-side electrode layer and an atmosphere-side electrode layer. The exhaust-side electrode layer is fixed on the outer surface of the solid electrolyte layer and the atmosphere-side electrode layer is fixed on the inner surface of the solid electrolyte layer.

In the driving circuit 60 (FIG. 5) for the oxygen sensor, the voltage supply circuits 66 and 67 and the current detecting circuit 68 for detecting the limit current is alleviated. The electromotive force characteristics of the oxygen sensor are changed by the constant current circuit 71 and the microcomputer 61 for outputting the current control signal to the constant current circuit 71.

In FIG. 14 showing a sensor driving routine executed by the microprocessor 61 employed in the sensor driving unit 60, the routine starts at the power-on time of the ECU 40 (sensor driving unit 60).

The microcomputer 61 carries out initialization processing at a step 500. In the initialization processing, the microcomputer 61 clears, among other things, activation flags F10, F11 and F12 representing the activation states of the oxygen sensor to "0". F10 is an inactivation flag which is set to "1" to indicate that the oxygen sensor is in an inactivated state. On the other hand, F11 is a semi-activation flag which is set to "1" to indicate that the oxygen sensor is in a semi-activated state. F12 is a complete activation flag which is set to "1" to indicate that the oxygen sensor is in a completely activated state.

The processing then moves on to a step 510 at which the microcomputer 61 sets the inactivation flag F10 to "1". Subsequently, the processing proceeds to a step 520 at which the microcomputer 61 determines whether the time lapsing since the start of the engine has exceeded a predetermined time T11. If the determination at the step 520 is NO, the processing returns to the step 510. If the determination at the step 520 is YES, on the other hand, the processing moves on to a step 530 at which the microcomputer 61 changes the electromotive force characteristics of the oxygen sensor. In the present embodiment, the electromotive force characteristics of the oxygen sensor are changed so that an air-fuel ratio point at which the electromotive force changes stepwisely is shifted from the stoichiometric air-fuel ratio point to the lean zone. Tat is, by flowing a forced current from the atmosphere-side electrode layer to the exhaust-side electrode layer, the air-fuel ratio point at which the electromotive force changes abruptly is shifted from the stoichiometric air-fuel ratio point to the lean zone.

Then, the processing moves on to a step 540 at which the semi-activation flag F11 is set to "1". Subsequently, the processing proceeds to a step 550 at which the microcomputer 61 determines whether the time lapsing since the start of the engine has exceeded a predetermined time T12. It should be noted that, when the semi-activation flag F11 is set to "1", the inactivation flag F10 is reset to "0".

If the determination at the step 550 is NO, the processing returns to the step 530. If the determination at the step 550 is YES, on the other hand, the processing moves on to a step 560 at which the electromotive force characteristics are shifted back or returned by the microcomputer 61 to its original characteristics by which the electromotive force changes stepwisely at the stoichiometric air-fuel ratio point. The processing then continues to a step 570 at which the complete activation flag F12 is set to "1" by the microcomputer 61. Thereafter, the present state is sustained as it is. It should be noted that, when the complete-activation flag F12 is set to "1", the semi-activation flag F11 is reset to "0".

Here, the values of the predetermined times T11 and T12 depend on whether or not the engine 1 is cold-started. The values of the predetermined times T11 and T12 may be in ranges from 0 to 10 seconds and from 0 to 20 seconds, respectively. In the case of a cold start of the engine 1, the predetermined times T11 and T12 are set at the upper limits of the ranges, 10 seconds and 20 seconds. If the engine is re-started after completion of the warming-up, on the other hand, the predetermined times T11 and T12 are all set to 0 second.

In this embodiment, the air-fuel ratio control routine is modifified as well as shown in FIG. 15. This routine is executed by the CPU 51 employed in the engine control unit 50 for each fuel injection, that is, at every 180 degrees CA.

As shown in the figure, the routine starts with a step 600 at which the CPU 51 reads in operating state of the engine such as the rotation speed Ne, the intake air pressure PM and the coolant temperature Thw from the sensors. The processing then moves on to a step 610 at which a basic injection quantity Tp from the rotation speed Ne of the engine and the intake air pressure PM is computed by using a basic injection map stored in the ROM 52. The processing then proceeds to a step 620 at which the CPU 51 determines whether the air-fuel ratio feedback conditions are satisfied. The air-fuel ratio feedback conditions include that the coolant temperature Thw is higher than a predetermined value and the engine is not in a high speed and heavy load state. If the air-fuel ratio feedback conditions are not satisfied (NO), the processing continues to a step 630 at which the CPU 51 implements air-fuel ratio open control, ending this routine.

If the air-fuel ratio feedback conditions are satisfied (YES) at the step 620, on the other hand, the processing continues to a step 640 at which the CPU 51 reads out the activation flags F10, F11 and F12 of the oxygen sensor set by the routine shown in FIG. 14 to determine if any of the flags is set to "1". Assuming that the inactivation flag F10 has been set to "1", the processing moves on to the step 630 at which the CPU 51 implements air-fuel-ratio open control, ending this routine.

If the inactivation flag F11 is "1", the processing moves on to a step 650 at which the CPU 51 implements feedback control of the air-fuel ratio based on a lean-side target air-fuel ratio of the oxygen sensor. After the processing carried out at the step 650 is finished, the routine is ended.

It should be noted that, for F11 =1, the oxygen sensor has characteristics which exhibit the stepwise change in electromotive force at an air-fuel ratio point shifted to the lean zone to a certain degree from the stoichiometric air-fuel ratio point. The CPU 51 implements the feedback control based on these characteristics.

If the complete activation flag F12 is set at "1", on the other hand, the processing moves on to a step 660 at which the CPU 51 implements feedback control of the air-fuel ratio based on the characteristics of the oxygen sensor which exhibit the stepwise change in electromotive force at the stoichiometric air-fuel ratio point, using the stoichiometric air-fuel ratio as a target air-fuel ratio. After finishing the processing carried out at the step 660, the present routine is ended.

As described with reference to the flowchart shown in FIG. 14, an air-fuel ratio point at which the electromotive force of the oxygen sensor changes stepwisely is shifted once to the lean zone. Of course, the air-fuel ratio point at which the electromotive force of the oxygen sensor changes can also be shifted to the rich zone. In the step 530 in FIG. 14, the air-fuel ratio point at which the electromotive force of the oxygen sensor changes abruptly can be shifted to the rich zone by reversely flowing a forced current from the exhaust-side electrode layer to the atmosphere-side electrode layer.

In particular, the present embodiment is different from the first to third embodiments in that, the electromotive force characteristics of an oxygen sensor of the electromotive force generating type are changed. Thus, also in the case of the present embodiment, there is provided an effect that, during the period till the oxygen sensor is heated to the completely activated state, the amount of exhausted HC is reduced.

(Fifth Embodiment)

Figure 16:
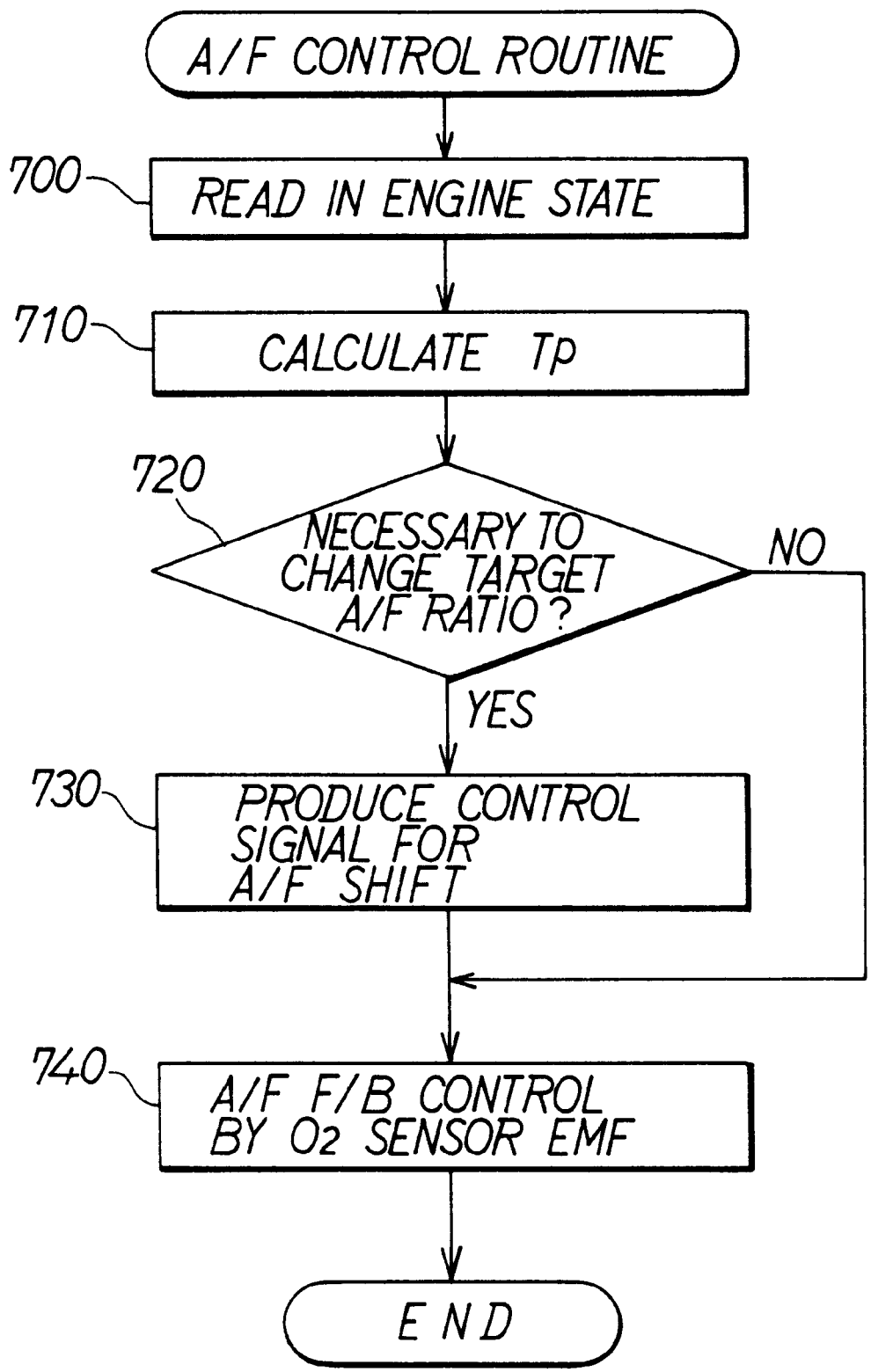
FIG. 16 a flowchart of an air-fuel ratio control routine executed in a fifth embodiment.

The fifth embodiment shown in FIG. 16 is a modification of the fourth embodiment (FIGS. 14 and 15) in respect of the feedback control of the air-fuel ratio after the completion of the warming-up, that is, after the activation of the sensor.

As shown in FIG. 16, the routine starts with a step 700 at which the CPU 51 reads in the operating state of the engine such as the rotation speed Ne, the intake air pressure PM and the coolant temperature Thw from the sensors. The processing then moves on to a step 710 at which a basic injection quantity Tp is calculated from the rotation speed Ne of the engine and the intake air pressure PM by using a basic injection map stored in the ROM 52.

The processing then proceeds to a step 720 at which the CPU 51 determines whether it is necessary to change the target air-fuel ratio from the present air-fuel ratio, typically, the stoichiometric air-fuel ratio point. The target air-fuel ratio needs to be changed because of some specific reasons. Typically, the target ratio is changed because the amount of injected fuel is increased due to acceleration of the vehicle or the amount of injected fuel is increased temporarily in order to prevent the three-way catalyst from being overheated. In this case, the target air-fuel ratio is shifted to the rich zone.

If the determination at the step 720 is YES, the processing moves on to a step 730 at which the CPU 51 outputs a control command signal to the sensor driving unit 60 (FIG. 5) for driving the oxygen sensor in order to request the sensor driving unit 60 to issue a current control signal to change the electromotive force characteristics of the oxygen sensor. In this case, in order to shift an air-fuel ratio point at which the electromotive force generated by the oxygen sensor changes stepwisely to the rich zone, as described above, it is necessary to flow a forced current from the exhaust-side electrode layer to the atmosphere-side electrode layer. In this way, the air-fuel ratio point at which the electromotive force generated by the oxygen sensor changes abruptly can be shifted to the rich zone. In order to shift an air-fuel ratio point at which the electromotive force generated by the oxygen sensor changes stepwisely to the lean zone, on the other hand, it is necessary to flow a forced current from the atmosphere-side electrode layer to the exhaust-side electrode layer. The processing then moves on to a step 740.

If the determination at the step 720 is NO, on the other hand, the processing bypasses the step 730, directly proceeding to the step 740 at which the CPU 51 implements feedback control of the air-fuel ratio based on the electromotive force output by the oxygen sensor. When the processing carried out at the step 740 is completed, this routine is terminated. It should be noted that the steps 730 and 740 of the flowchart shown in FIG. 16 changes a sensor characteristics and controls an air-fuel ratio.

As described above, according to the fifth embodiment, feedback control of the air-fuel ratio at an air-fuel ratio point shifted away from the stoichiometric air-fuel ratio point can be implemented, allowing the noxious exhaust emission to be reduced and the good drivability to be maintained. That is, feedback control of the air-fuel ratio at an air-fuel ratio point in the lean or rich zone can be implemented even if an oxygen sensor having only electromotive force characteristics exhibiting a stepwise change in electromotive force at the stoichiometric air-fuel ratio point is employed for oxygen concentration detection.

(Modified Embodiment)

The foregoing embodiments may be further modified as follows.

(1) In the case of the first to third embodiments described above, in the determination of the activation state of the air-fuel ratio sensor 26, the state of activation is divided into three states: the semi-activated state, the substantially activated state and the completely activated state. It should be noted, however, that the determination can also be made by dividing the state into at least the semi-activated state and the completely activated state. For example, at the step 150 in the first embodiment in FIG. 7, the microcomputer 61 determines whether the sensing element resistance RS is equal to or smaller than the second criterion value R2 (RS≦R2). If the sensing element resistance RS is equal to or smaller than the second criterion value R2, the switch circuits 69 and 70 shown in FIG. 5 are switched over to a state of applying voltages to the air-fuel ratio sensor 26 and the complete activation flag F3 is set to "1". In this case, the steps 170 and 180 are eliminated. In a similar way, the steps 310 and 410 in the second and third embodiments shown in FIGS. 12 and 13 respectively are each changed to processing to determine whether the air-fuel ratio sensor 26 is in a completely activated state. As the determination at the step 310 or 410 becomes YES, the switch circuits 69 and 70 shown in FIG. 5 are switched over to a state of applying voltages to the air-fuel ratio sensor 26 and the complete activation flag F3 is set to "1". In this case, the steps 170, 320 and 420 are eliminated. In addition, the step 260 in the air-fuel ratio control routine shown in FIG. 9 to implement feedback control of the air-fuel ratio in a substantially activated state of the air-fuel ratio sensor 26 after the feedback conditions are satisfied at the step 240 is also eliminated. The CPU 51 implements feedback control of the air-fuel ratio only in a semi-activated state or a completely activated state of the air-fuel ratio sensor 26 at the step 250 or 270 respectively.

Figure 17:
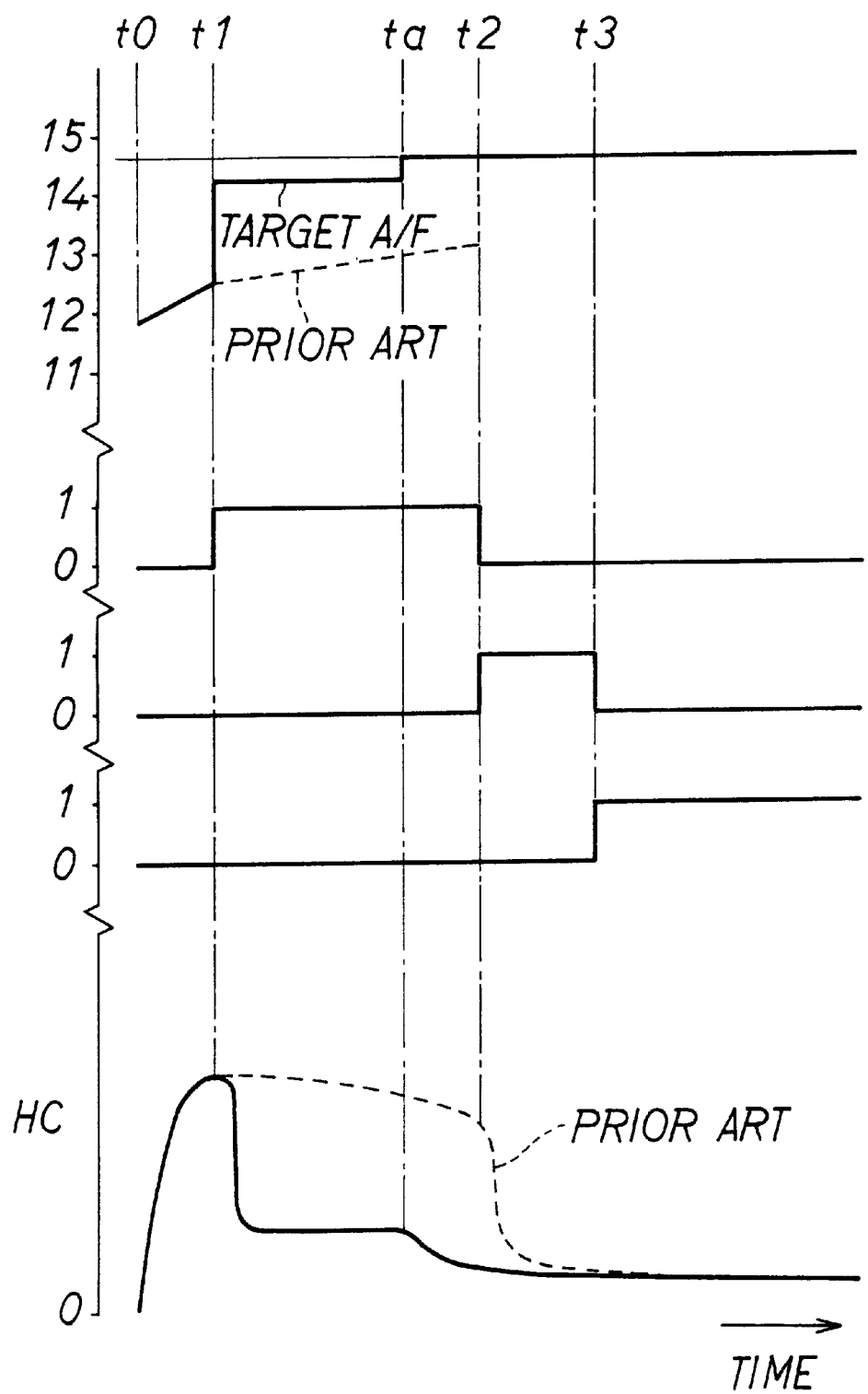
FIG. 17 is a time chart showing operations of feedback control in another embodiment.

(2) In the operation of the first embodiment shown in FIG. 11, the target air-fuel ratio is set on the lean side in a semi-activated state of the air-fuel ratio sensor 26. Depending upon the characteristics of the engine, feedback control can of course be implemented on the rich side as shown in FIG. 17. That is, at a point of time t1 at which the semi-activation flag F1 is set, the target air-fuel ratio is set to a point in close proximity to the stoichiometric air-fuel ratio point to a certain degree on the rich side. Later on, at a point of time ta at which the engine runs in a stable state, the target air-fuel ratio is changed to the stoichiometric air-fuel ratio point. In this case, even for an engine having characteristics which do not indicate rotation in a stable manner in the lean zone right after a start, by implementing feedback control at a desired target air-fuel ratio early, the amount of exhausted HC can also be reduced.

(3) As described above, in the case of the first to third embodiments, a variety of criteria for a determination on the activation state of the air-fuel ratio sensor 26 are set. It should be noted, however, that criteria for a determination on the activation state of the air-fuel ratio sensor 26 are not limited thereto. Other criteria can also be adopted. For instance, the time lapsing since the start of the engine, the level of the electromotive force generated by the air-fuel ratio sensor 26, the sensing element resistance RS of the air-fuel ratio sensor 26, the sensing element temperature of the air-fuel ratio sensor 26, the amount of electric power supplied by the heater 33 provided on the air-fuel ratio sensor 26 since the start of the engine or combinations of them can be used as a base for a determination on the activation state of the air-fuel ratio sensor. This criteria may also used in the fourth embodiment.

(4) The foregoing embodiments each implement an air-fuel ratio control apparatus employing an oxygen sensor or an air-fuel ratio, both using a cup-shaped solid electrolyte. In place of these sensors, a plate-layer type air-fuel ratio sensor, that is, a plate-layer oxygen sensor or a plate-layer air-fuel ratio, can also be used. Also in this case, in a semi-activated state of the air-fuel ratio sensor, a forced current is flowed from the reference-side electrode layer (atmosphere-side electrode layer) to the measured-side electrode layer (exhaust-side electrode layer) provided on both sides of the stack-type solid electrolyte layer or vice versa in order to shift the air-fuel ratio point, at which the electromotive force generated by the air-fuel ratio sensor changes stepwisely, is shifted from the stoichiometric air-fuel ratio point to the lean or rich zone, respectively. Then, feedback control of the air-fuel ratio based on the shifted electromotive force characteristics is implemented.

(5) Even though one pair of such electrode layers provided on both sides of the solid state electrolyte layer of the air-fuel ratio sensor are sufficient, a plurality of pairs can also be furnished.

(Sixth Embodiment)

A sixth embodiment is directed particularly to the construction of the air-fuel ratio sensor 26 of the limit current type. This sensor may be used in the foregoing first to fifth embodiments as well.

Figure 18:
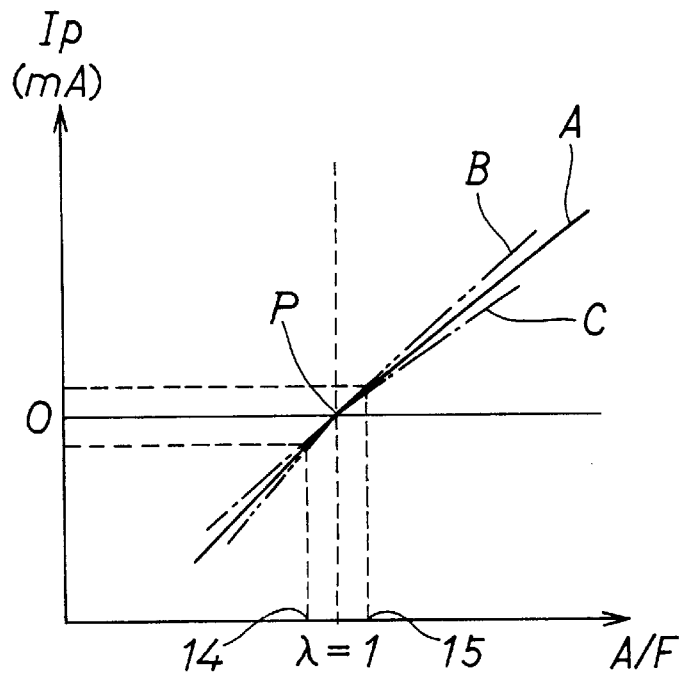
FIG. 18 is a chart showing relations between an air-fuel ratio A/F and a limit current Ip of an air-fuel ratio sensor of the limit current type in a sixth embodiment.
Figure 19:
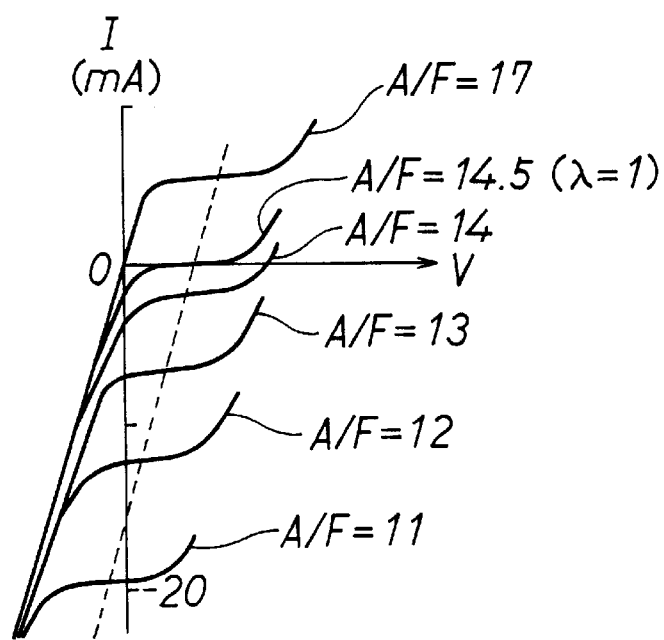
FIG. 19 is a chart showing relations between an applied voltage and an output current of the air-fuel ratio sensor of the limit current type in the sixth embodiment.

It is desired that the air-fuel ratio sensor exhibits the characteristics shown in FIGS. 18 and 19. As understood from FIG. 18 showing output characteristics of three different air-fuel ratio sensors 26 (A, B and C), that is, relations between the air-fuel ratio A/F and the limit current, the limit current Ip output by each of the air-fuel ratio sensors changes smoothly and linearly with the air-fuel ratio A/F in the zones on both sides of the stoichiometric air-fuel ratio point ($\lambda=1$) which serves as a border between both the zones.

Therefore, the deviation of the air-fuel ratio A/F from the stoichiometric air-fuel ratio point ($\lambda=1$) which may be used as a feedback control target can be detected from the limit current Ip with a high degree of accuracy. By feeding back the limit current Ip representing the actual air-fuel ratio A/F in the air-fuel ratio control, the air-fuel ratio A/F can be controlled with good response characteristics and with a high degree of accuracy. Since the atmospheric air is used as a reference, the output of the air-fuel ratio sensor is stable.

As understood from FIG. 19 showing the relation between a voltage V applied between the atmosphere-side electrode layer and the exhaust-side electrode layer and the current I of the air-fuel ratio sensor 26 of the limit current type for different air-fuel ratios A/F, the current I remains unchanged in a certain range of the applied voltage for each air-fuel ratio A/F. This value is referred to as the limit current Ip shown in FIG. 18. This unchanged portion of each of the curves indicates that, even if the applied voltage varies, the current I is maintained at the limit current Ip, resulting in a high detection accuracy. The air-fuel ratio sensor 26 in this embodiment is so constructed to cause the limit current Ip to zero (Ip=0) at the stoichiometric air-fuel ratio A/F of 14.5 ($\lambda=1$), so that control of the air-fuel ratio A/F with the zero limit current Ip (Ip=0) taken as a reference can be carried out with ease. It should be noted that the relations between the air-fuel ratio A/F and the limit current Ip are the same as relations between the air-fuel ratio A/F and the limit current Ip, that is, the coordinates of cross points of a dashed line and the curves shown in FIG. 19.

Figure 20:
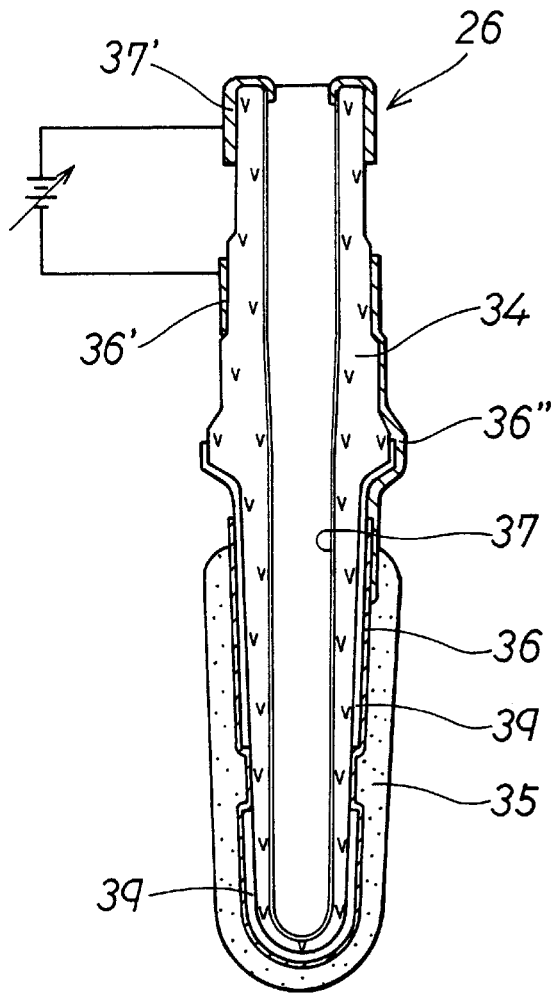
FIG. 20 is a cross sectional view showing the air-fuel ratio sensor of the limit current type in the sixth embodiment.

In this embodiment, as shown in FIG. 20, the air-fuel ratio sensor 26 of the limit current type is constructed as a single cell type. The sensor 26 comprises a solid electrolyte layer (sensing element) 34 with a shape resembling a cup made of an oxygen ion conductive material, the atmosphere-side electrode layer 37 provided on the hollow inner side of the solid electrolyte layer 34 in contact with the atmospheric air and an exhaust-side electrode layer 36 provided on the other side of the solid electrolyte layer 34 in contact with gas exhausted by the engine. A voltage is applied between the atmosphere-side electrode layer 37 and the exhaust-side electrode layer 36 and a current flowing from the atmosphere-side electrode layer 37 to the exhaust-side electrode layer 36 or vice versa is detected. It should be noted that the atmosphere-side electrode layer 37 is electrically connected to a terminal portion 37' of the opening end of the solid electrolyte layer 34 and the exhaust-side electrode layer 36 is connected to the terminal portion 36' through a lead portion 36". The exhaust-side electrode layer 36 has a reduced diameter on a portion of the sensor that generates the limit current. This reduced diameter portion is brought into a direct contact with the solid electrolyte layer 34. The remaining portion is attached to the solid electrolyte layer 34 through an electrical insulating layer 39. On the surface of the exhaust-side electrode layer 36, a porous diffused resistor layer 35 is provided. It should be noted that the solid electrolyte layer 34 is made of a $ZrO_2$—$Y_2O_3$ material whereas the atmosphere-side electrode layer 37 and the exhaust-side electrode layer 36 are provided by Pt-plating technique. The thickness of the sensor is about 5 mm.

The sensor 26 has the solid electrolyte having an open end and a closed end. Therefore, even if the sensor temperature is raised rapidly by a heater, heat stress does not concentrate assuring a higher reliability than in the case of using a plate-shaped solid electrolyte.

Figure 21:
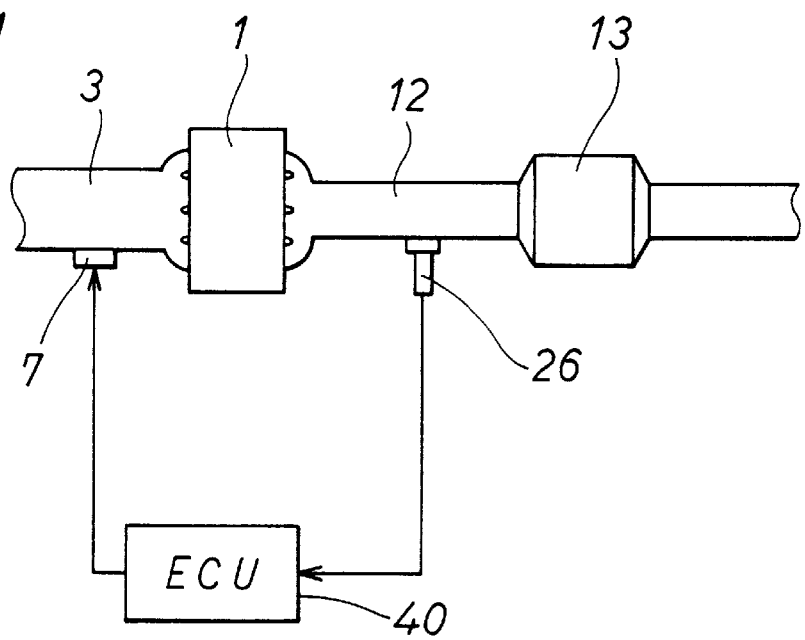
FIG. 21 is a schematic view showing an air-fuel ratio control apparatus according to the sixth embodiment.

This sensor 26 is used as shown in FIG. 21, in the similar manner as in the foregoing embodiments or specifically for the feedback control to the stoichiometric air-fuel ratio.

Assume that the limit current Ip corresponds to an air-fuel ratio A/F of 15 (lean zone) as shown in FIG. 18. In this case, the air-fuel-ratio control apparatus 40 operates in accordance with the limit current Ip so as to increase the amount of fuel supplied by the fuel injection valve 7. Thus, the concentration of oxygen in the exhausted gas is gradually reduced. As a result, the limit current Ip generated by the air-fuel ratio sensor 26 of the limit current type becomes zero, controlling the air-fuel ratio to the stoichiometric air-fuel ratio ($\lambda$=1). If the limit current Ip corresponds to an air-fuel ratio A/F of 14 (rich zone), on the other hand, the ECU 40 operates in accordance with the limit current Ip so as to decrease the amount of fuel supplied by the fuel injection valve 7. As a result, the limit current Ip generated by the air-fuel ratio sensor 26 of the limit current type likewise becomes zero, similarly controlling the air-fuel ratio to the stoichiometric air-fuel ratio ($\lambda$=1). In this way, according to the air-fuel ratio control method adopted by the present embodiment, the air-fuel ratio can be controlled to the stoichiometric air-fuel ratio ($\lambda$=1) with a high degree of accuracy and a high degree of reliability.

The air-fuel ratio sensor 26 shown in FIG. 20 was tested with respect to its various operating characteristics and its test results are shown in FIGS. 22 to 26.

Figure 22:
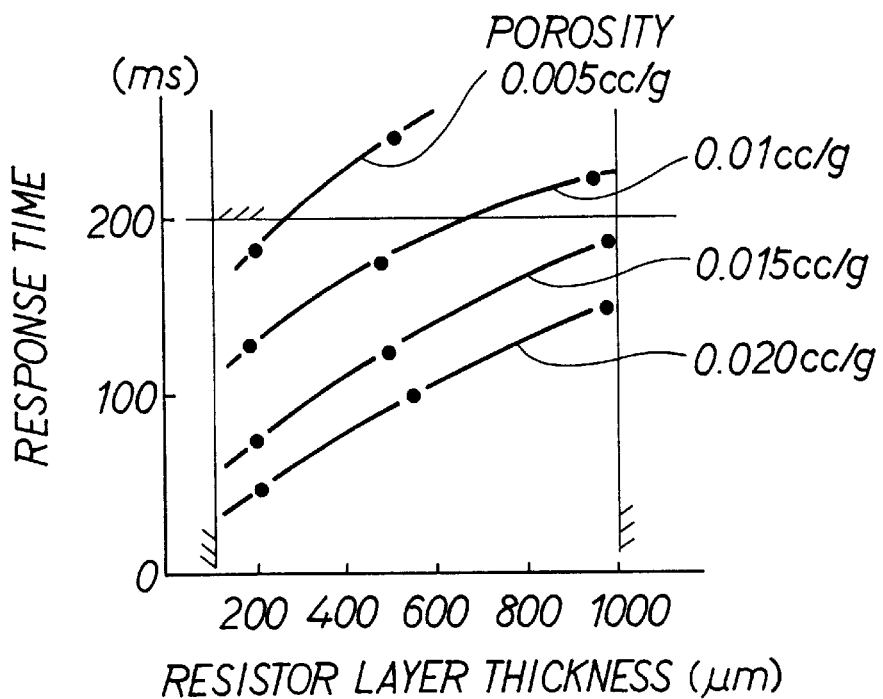
FIG. 22 is a chart showing relations between a thickness and a response time of a diffused resistor layer of the air-fuel ratio sensor of the limit current type.

First, there exists a relation between the thickness [$\mu$m] of the porous diffused resistor layer 35 and the response time [ms] of the limit current type air-fuel ratio sensor 26 as shown in FIG. 22, with the diffused resistor layer 35 being made of spinel powder and provided by a plasma spraying technique. The data in FIG. 22 was measured by changing the porosity (fine aperture volume cc/g) of the diffused resistor layer 35.

It is obvious from the relations shown in FIG. 22 that, in order to reduce the response time to a value smaller than 200 ms (milliseconds) in the air-fuel ratio sensor of the limit current type, it is necessary to set the porosity at a value in the range 0.005 to 0.020 cc/g. It should be noted that, in the case of a porosity greater than 0.020 cc/g, the diffused resistor layer 35 does not function sufficiently to provide the linear output of the limit current is lost.

In addition, it is desirable to set the thickness of the diffused resistor layer 35 at a value in the range 100 to 1,000 microns. For a thickness smaller than 100 microns, as an electrode protecting layer, the diffused resistor layer 35 is hardly useful. In the case of a thickness greater than 1,000 microns, on the other hand, it is likely that the heat resistance characteristics and the shockproof property degrades.

Figure 23:
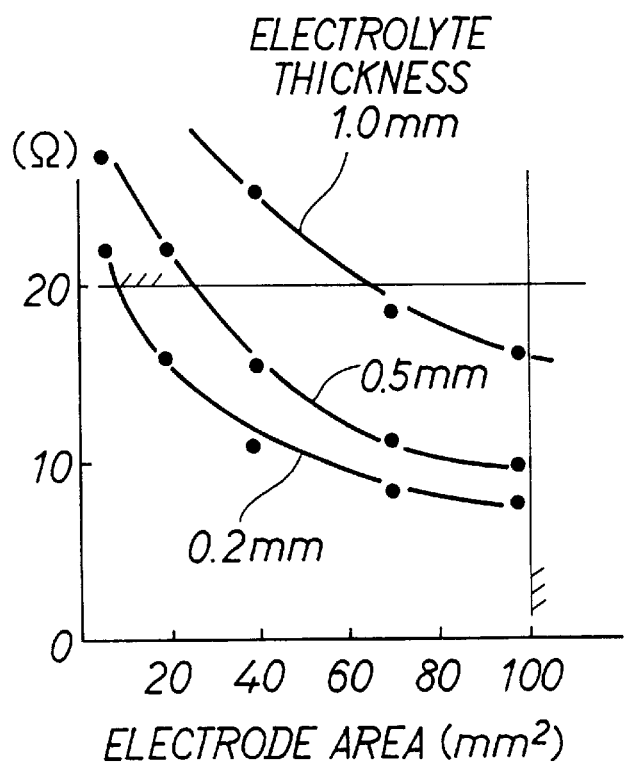
FIG. 23 is a chart showing relations between a sensing element resistance and an electrode area of the air-fuel ratio sensor of the limit current type in the sixth embodiment.
Figure 24:
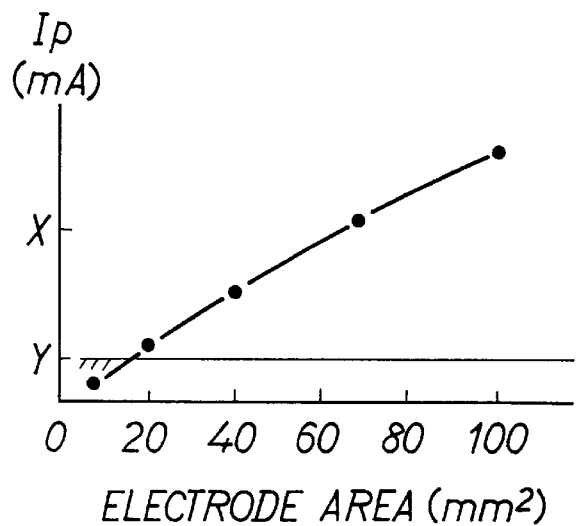
FIG. 24 is a chart showing a relation between an electrode area and a limit current of the air-fuel ratio sensor of the limit current type.
Figure 25:
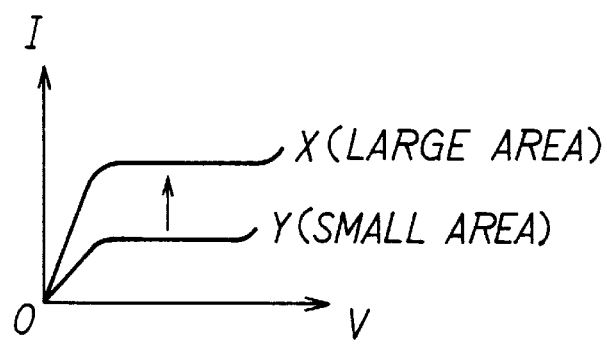
FIG. 25 is a chart showing relations between an applied voltage area and an output current of the air-fuel ratio sensor of the limit current type.
Figure 26:
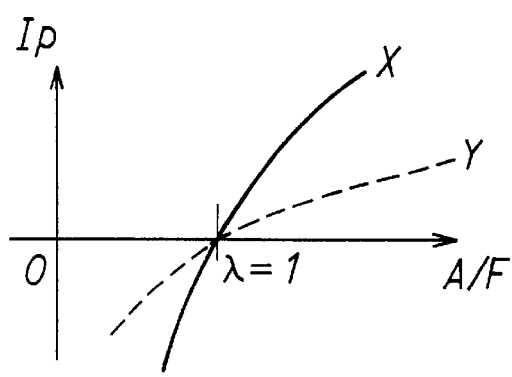
FIG. 26 is a chart showing relations between an air-fuel ratio and a limit current of the air-fuel ratio sensor of the limit current type.

The sensor 26 exhibits, as shown in FIG. 23, a relation between the electrode area [$mm^2$] and the sensing element resistance [$\Omega$] with the thickness of the solid-state electrolyte layer [mm] taken as a parameter. It also exhibits, as shown in FIGS. 24 and 25, a relation between the electrode area [$mm^2$] and the limit current and a relation between the voltage applied thereto type and the output current with the electrode area taken as a parameter. In a case Y shown in FIG. 25 in which the electrode area is small, the value of the limit current is also small. In a case X in which the electrode area is large, the value of the limit current is also large. Finally, the sensor exhibits as shown in FIG. 26 a relation between the air-fuel ratio A/F and the limit current Ip for the cases X and Y of FIG. 25.

As obvious from these relations, in the air-fuel ratio sensor of the limit current type, it is desirable to set the electrode area at a value in the range 20 to 100$mm^2$. In the case of an electrode area smaller than 20 $mm^2$, the sensing element resistance is large so that the output limit current is small. In the case of an electrode area greater than 100 $mm^2$, on the other hand, it is likely that the time it takes to activate the solid state electrolyte layer after the start of the engine is long. It is also obvious that a thickness of the solid electrolyte layer in the range 0.2 to 1 mm is desirable. A thickness of the solid electrolyte layer smaller than 0.2 mm has a durability problem. On the other hand, a thickness of the solid electrolyte layer greater than 1.0 mm has a problem that it is likely that the sensing element internal resistance increases as shown in FIG. 23.

According to the sixth embodiment, unlike an air-fuel ratio sensor of the dual cell oxygen-pump type, since the air-fuel ratio sensor 26 does not have a measurement gas chamber, the response characteristics thereof is good, allowing the exhaust gas to be cleaned well even if the three-way catalyst has deteriorated to a certain degree.

The air-fuel ratio sensor 26 may also be used as well at the downstream of the three-way catalytic converter 13. In this arrangement, the air-fuel ratio represented by the limit current Ip can be detected with respect to the exhaust gas cleaned by the converter 13 so that the air-fuel ratio may be feedback controlled to the stoichiometric ratio with a higher reliability. Even if the three-way catalyst in the converter 13 deteriorates resulting in a change of an air-fuel ratio range where the catalyst exhibits a high purification ability, this change can be detected by the air-fuel ratio sensor 26.

The present invention having been described with reference to various embodiments may be modified further in various ways without departing from the spirit of the invention.

What is claimed is:

1. An air-fuel ratio control apparatus comprising:

an air-fuel ratio sensor having a solid electrolyte layer and at least a pair of electrodes provided on both sides of said solid electrolyte layer, said air fuel ratio sensor being constructed to generate an electromotive force which changes stepwisely in a zone in close proximity to a stoichiometric air-fuel ratio point when no forced current is supplied thereto externally;

sensor characteristics changing means for changing electromotive force generating characteristics of said air-fuel ratio sensor to characteristics with an air-fuel ratio point, at which said electromotive force changes stepwisely, shifted from said stoichiometric air-fuel ratio point to one of a lean and a rich zone by a forced current from one of said electrodes to the other electrode of said air-fuel ratio sensor; and air-fuel ratio control means for implementing feedback control of an air-fuel ratio by using said electromotive force characteristics changed by said sensor characteristics changing means, said changed electromotive force generating characteristics being used for determining whether an actual air-fuel ratio is in said one of a lean and a rich zone.

2. An air-fuel ratio control apparatus comprising:

an air-fuel ratio sensor having a solid electrolyte layer and at least a pair of electrodes provided on both sides of said solid electrolyte layer, said air-fuel ratio sensor being constructed to generate an electromotive force which changes stepwisely in a zone in close proximity to a stoichiometric air-fuel ratio point when no forced current is supplied thereto externally;

activation state determining means for determining whether said air-fuel ratio sensor is in one of a semi-activated state and a completely activated state;

sensor characteristics changing means for changing electromotive force generating characteristics of said air-fuel ratio sensor when said determining means determines that said air-fuel ratio sensor is in said semi-activated state, said electromotive force generating characteristics being changed to characteristics with an air-fuel ratio point at which said electromotive force changes stepwisely, shifted from said stoichiometric air-fuel ratio point to one of a lean and a rich zone by a forced current supplied thereto externally from one of said electrodes to the other electrode;

first air-fuel ratio control means for implementing feedback control of an air-fuel ratio by using said electromotive force characteristics changed by said sensor characteristics changing means when said determining means determines that said air-fuel ratio sensor is in said semi-activated state, said electromotive force generating characteristics being used for determining whether an actual air-fuel ratio is in said one of a lean and a rich zone with respect to said air-fuel ratio point of said electromotive force generating characteristics at which said electromotive force changes stepwisely; and second air-fuel ratio control means for implementing feedback control of said air-fuel ratio by using an air-fuel ratio detected by said air-fuel-ratio sensor when said determining means determines that said air-fuel ratio sensor is in said completely activated state.

3. An air-fuel ratio control apparatus according to claim 2, wherein:

said electrodes of said air-fuel ratio sensor are exposed to a reference gas and a measured gas; and said sensor characteristics changing means changes said electromotive force generating characteristics of said air-fuel ratio sensor to characteristics with an air-fuel ratio point at which said electromotive force changes stepwisely, shifted from said stoichiometric air-fuel ratio point to a lean zone by said forced current from said electrode on a side of said reference gas to said electrode on a side of said measured gas, or to a rich zone by said forced current from said electrode on said side of said measured gas to said electrode on said reference gas.

4. An air-fuel ratio control apparatus according to claim 2, wherein:

said air-fuel ratio sensor has first characteristics which exhibit said electromotive force generating characteristics of stepwise change at said stoichiometric air-fuel ratio point when no voltage is applied between said electrodes, and second characteristics which exhibit linear changes in current output with changes in said air-fuel ratio when a predetermined voltage is applied between said electrodes; and said sensor characteristics changing means changes said first characteristics by controlling a current flowing from one of said electrodes to the other electrode of said air-fuel ratio sensor.

5. An air-fuel ratio control apparatus according to claim 4, wherein:

said first air-fuel ratio control means implements feedback control of said air-fuel ratio based on said first characteristics changed by said sensor characteristics changing means; and said second air-fuel ratio control means implements feedback control of said air-fuel ratio based on said second characteristics.

6. An air-fuel ratio control apparatus according to claim 2, wherein:

said activation state determining means is for determining said activation state of said air-fuel ratio sensor based on at least one of a time lapsing since a start of an internal combustion engine, a level of said electromotive force generated by said air-fuel ratio sensor, a resistance of said solid electrolyte layer, a temperature of said solid electrolyte layer and an amount of power supplied to a heater provided in said air-fuel ratio sensor since said start of said internal combustion engine.

7. An air-fuel ratio control method for an engine having an air-fuel ratio sensor disposed in an exhaust gas and having a solid electrolyte layer and a pair of electrodes provided on both sides of said solid electrolyte layer for generating an electromotive force which changes stepwisely around a stoichiometric air-fuel ratio point, said air-fuel ratio control method comprising the steps of:

supplying a forced electric current to said air-fuel ratio sensor through said electrodes externally for changing electromotive force generating characteristics of said air-fuel ratio sensor to characteristics in which said electromotive force changes stepwisely at a point shifted from said stoichiometric air-fuel ratio point; and implementing a feedback control of an air-fuel ratio to an air-fuel ratio other than said stoichiometric air-fuel ratio by using said changed electromotive force characteristics.

8. An air-fuel ratio control method according to claim 7 further comprising the steps of:

determining an activation state of said air-fuel ratio sensor for determining whether said air-fuel ratio sensor is in one of a semi-activated state and a completely activated state;

enabling said forced electric current supplying step and said feedback control implementing step in response to a determination that said air-fuel ratio sensor is in said semi-activated state; and disabling said forced electric current supplying step and said feedback control implementing step in response to a determination that said air-fuel ratio sensor is in said completely activated state.

9. An air-fuel ratio control method according to claim 8, further comprising the steps of:

supplying a voltage to said air-fuel ratio sensor through said electrodes externally in response to a determination that said air-fuel ratio sensor is in said completely activated state, said air-fuel ratio sensor producing a limit current proportional to an air-fuel ratio when supplied with said voltage; and implementing another feedback control of an air-fuel ratio to an air-fuel ratio point different from said shifted air-fuel ratio point by using said limit current.

10. An air-fuel ratio control method according to claim 7, further comprising the steps of:

supplying a voltage to said air-fuel ratio sensor through said electrodes externally after said forced current supplying step, said air-fuel ratio sensor producing when supplied with said voltage a limit current proportional to an air-fuel ratio different from said shifted air-fuel ratio point; and implementing another feedback control of an air-fuel ratio to said air-fuel ratio different from said shifted air-fuel ratio point by using said limit current.

11. An air-fuel ratio control method for controlling an air-fuel ratio of an air-fuel mixture supplied to an internal combustion engine to a stoichiometric air-fuel ratio, said method comprising the steps of:

providing a single cell air-fuel ratio sensor having a solid electrolyte capable of conducting oxygen ions, a first electrode provided on one side of said solid electrolyte in contact with an atmosphere and a second electrode provided on an other side of said solid electrolyte in contact with gas exhausted by said internal combustion engine;

detecting limit current produced by said air-fuel ratio sensor by applying a predetermined voltage between said first and second electrodes, said limit current representing the concentration of oxygen contained in said gas exhausted by said internal combustion engine or the concentration of unburned gases; and controlling said air-fuel ratio of said mixture so that said limit current becomes zero.

12. An air-fuel ratio control method according to claim 11, wherein:

said air-fuel ratio sensor is constructed to produce at least 10 mA as said limit current when said oxygen concentration is 7.5%.

13. An air-fuel ratio control method according to claim 11, wherein:

said solid electrolyte is in a cup shape having a closed end and an open end.

14. An air-fuel ratio control method according to claim 11, wherein:

said air-fuel ratio sensor is disposed downstream of a three-way catalytic converter.

15. An air-fuel ratio control apparatus for controlling an air-fuel ratio, comprising:

an air-fuel ratio sensor that generates an electromotive force that changes in a step-wise manner in a first zone around a stoichiometric air-fuel ratio point;

a characteristic shifting circuit configured to shift the zone in which the electromotive force changes in a step-wise manner from the first zone around the stoichiometric air-fuel ratio point to a second zone, wherein the second zone is either a lean zone or a rich zone; and a feedback control circuit configured to implement feedback control of said air-fuel ratio sensor using an air-fuel ratio point in the second zone as a target air-fuel ratio in at least one operational state of said air-fuel ratio sensor.

16. An air-fuel control apparatus according to claim 15, wherein said feedback control circuit is configured to implement feedback control of said air-fuel ratio sensor using the air-fuel ratio point in the second zone as a target air-fuel ratio when said air-fuel ratio sensor is operated in a semi-activated state.

17. An air-fuel control apparatus according to claim 15, wherein said air-fuel ratio sensor is positioned in an exhaust system of an internal combustion engine.

18. A method of controlling an air-fuel ratio, comprising:

shifting a zone in which an electromotive force generated by an air-fuel ratio sensor changes in a step-wise manner from a first zone around a stoichiometric air-fuel ratio point to a second zone, wherein the second zone is either a lean zone or a rich zone; and using an air-fuel ratio point in the second zone as a target air-fuel ratio in at least one operational state of said air-fuel ratio sensor.

19. A method according to claim 18, wherein the air-fuel ratio point in the second zone is used as a target air-fuel ratio when said air-fuel ratio sensor is operated in a semi-activated state.

* * * * *